(12) United States Patent
Adams et al.

(10) Patent No.: US 12,234,408 B2
(45) Date of Patent: Feb. 25, 2025

(54) PHOTOCHROMIC AND ELECTROCHROMIC COMPOUNDS

(71) Applicant: The University Court of the University of Glasgow, Strathclyde (GB)

(72) Inventors: Emily Rose Adams, Strathclyde (GB); David John Adams, Strathclyde (GB)

(73) Assignee: The University Court of the University of Glasgow Glasgow, Strathclyde (GB)

(*) Notice: Subject to any disclaimer, the term of this patent is extended or adjusted under 35 U.S.C. 154(b) by 687 days.

(21) Appl. No.: 17/272,616

(22) PCT Filed: Aug. 30, 2019

(86) PCT No.: PCT/EP2019/073249
§ 371 (c)(1),
(2) Date: Mar. 1, 2021

(87) PCT Pub. No.: WO2020/043895
PCT Pub. Date: Mar. 5, 2020

(65) Prior Publication Data
US 2021/0349367 A1    Nov. 11, 2021

(30) Foreign Application Priority Data

Aug. 30, 2018 (GB) .................................... 1814093

(51) Int. Cl.
G02F 1/1516    (2019.01)
C07D 471/06    (2006.01)
C09K 9/02      (2006.01)

(52) U.S. Cl.
CPC .............. *C09K 9/02* (2013.01); *C07D 471/06* (2013.01); *C09K 2211/1018* (2013.01); *G02F 1/1516* (2019.01)

(58) Field of Classification Search
CPC .. G02F 1/1516; C09K 9/02; C09K 2211/1018
See application file for complete search history.

(56) References Cited

U.S. PATENT DOCUMENTS

2012/0101022 A1    4/2012    Tovar

FOREIGN PATENT DOCUMENTS

| CN | 103596966 A | 2/2014 | |
| EP | 1340755 A1 * | 9/2003 | ........... C07D 471/06 |

(Continued)

OTHER PUBLICATIONS

Sheng-Huei Hsiao, Yi-Zhi Chen, Electroactive and ambipolar electrochromic polyimides from arylene diimides with triphenylamine N-substituents, Dyes and Pigments 144 (2017) 173-183. (Year: 2017).*

(Continued)

*Primary Examiner* — Bijan Ahvazi
(74) *Attorney, Agent, or Firm* — Stites & Harbison PLLC; Richard S. Myers, Jr.

(57) ABSTRACT

Provided are novel naphthalene diimide (NDI) compound of Formula 1. The compounds may exhibit colour change from substantially transparent to substantially black upon electrochemical or photochemical stimulus and may be useful in smart windows.

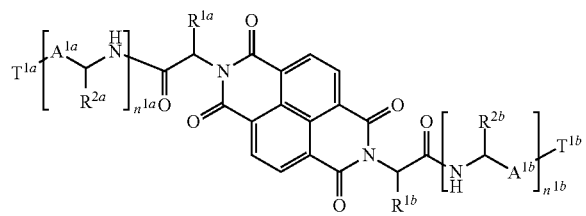

19 Claims, 11 Drawing Sheets

(56) References Cited

FOREIGN PATENT DOCUMENTS

| JP | 2014-029502 | 2/2014 |
|---|---|---|
| WO | WO2002-040479 | 5/2002 |

OTHER PUBLICATIONS

Veerababu Medabalmi, Nirmalendu Kuanr, and Kothandaraman Ramanujam, Reversible Sodium Storage Behavior of Aromatic Diimide Disodium Carboxylatesn Journal of The Electrochemical Society, 164 (1) A6147-A6153 (2017). (Year: 2017).*

Al Kobaisi et al., "Functional Naphthalene Diimides: Synthesis, Properties, and Applications", Chem. Rev., 2016, vol. 116, pp. 11685-11796.

Boer et al., "Engineering entanglement: controlling the formation of polycatenanes and polyrotaxanes using π interactions", Chem. Commu., 2014, vol. 50, pp. 1125-1127.

Bornhof et al., "Synergistic Anion-(π)n-π Catalysis on π-Stacked Foldamers", J. Am. Chem. Soc., 2018, vol. 140, pp. 4884-4892.

Datta et al., "Near instantaneous gelation of crude oil using naphthalene diimide based powder gelator", J. Mater. Chem. A, 2018. vol. 6, pp. 2922-2926.

Fierx-David et al., "Uber die Darstellung con Naphthoylenimidazolinen", Helv. Chim. Acta, 1938, vol. 21, pp. 1466-1489.

Parveen et al., "Simple Organic Salts Having a Naphthalenediimide (NDI) Core Display Multifunctional Properties: Gelation, Anticancer and Semiconducting Properties", Chem. Asian. J., 2018, vol. 13, pp. 170-180.

Hsiao et al., "Electroactive and ambipolar electrochromic polyimides from arylene diimides with triphenylamineN- substituents", Dyes and Pigments, 2017, vol. 144, pp. 173-183.

Tambara et al., "Conversion of aldoximes into nitriles and amides under mild conditions", Org. Biomol. Chem., 2013, vol. 11, pp. 2466-2472.

Search Report of the UKIPO for GB 1814093.9 dated Mar. 18, 2019.

International Search Report and Written Opinion of the International Searching Authority for PCT/EP2019/073249 dated Oct. 17, 2019.

International Preliminary Report on Patentability for PCT/EP2019/073249 dated Mar. 2, 2021.

Alkaabi, et al., Transparent-to-Dark Electrochromic Behavior in Naphthalene-Diimide-Based Mesoporous MOF-74 Analogs, Chem 1, 264-272, Aug. 11, 2016.

Zheng, et al., Near-Infrared Electrochromic and Chiroptical Switching Materials: Design, Synthesis, and Characterization of Chiral Organogels Containing Stacked Naphthalene Diimide Chromophores, Chem. Mater. 2008, 20, 6163-6168.

Koujiro et al., Organic & Biomolecular Chem., vol. 11., 2466 (2013).

Registry(STN)[online] Dec. 12, 2017 RN2156643-46-6, Jun. 8, 2008 RN1026291-99-5, Sep. 7, 2004 RN741206-45-1.

Pandeeswar et al., "Bioinspired Nanoarchitectonics of Napthalene Diimide to Acess 2D sheets of Tunable Size, Shape and Optoelectonic Properties", J Inorg Organomet Polym.

Andric et al, "Spectoscopy of Napthalene Diimides and Their Anion Radicals", Aust. J. Chem. 57.

JP2021-510416—Notice of Reasons for Rejection Sep. 12, 2023—JP first office action.

CN201980070402.X—search report Oct. 31, 2023—CN search report.

* cited by examiner

PHOTOCHROMIC AND ELECTROCHROMIC COMPOUNDS

CROSS REFERENCE TO RELATED APPLICATIONS

This application is a § 371 National State Application of PCT/EP2019/073249 filed Aug. 30, 2019, which claims priority to GB 1814093.9 filed Aug. 30, 2018.

RELATED APPLICATION

The present case claims priority to, and the benefit of, UK Patent Application, GB 1814093.9, filed on 30 Aug. 2018 (30 Aug. 2018), the contents of which are hereby incorporated by reference in their entirety.

FIELD OF THE INVENTION

The present invention relates to the field of photochromic and electrochromic compounds and compositions thereof. In particular, the present invention relates to such compounds that are suitable for use in smart windows.

BACKGROUND

Electrochromic materials change colour when a current is applied. These materials can be used for applications such as smart windows, wherein the transmittance is controlled, allowing for privacy and energy efficiency benefits.

It is desirable for the transition to be fast, reversible over many cycles, and of the correct colour change, and the materials to be cost-effective (for example, in terms of synthesis and in needing little power to effect the colour change) and easily processable.

Many electrochromic materials are based on inorganic materials such as transition metal oxides. These materials are effective in terms of operation but the processing and coating methods are generally energy intensive. Metal electrodeposition has also been used.

Some organic materials have also been shown to be effective electrochromic materials. Such materials may have advantages including solution processability, low switching times, colour tunability, and high colouration.

It is challenging for electrochromic materials, in particular when used in smart windows, to achieve neutral shades such as grey and black from a film with a transparent initial state. For this reason, many polymer films, for example, have a coloured initial state as well as a coloured final state.

Transmissive-to-black electrochromic materials are more difficult to form. This is at least partly due to the difficulty in controlling the absorption properties of the redox states such that a black colour is provided. Typical examples of materials that exhibit a black state are certain polymer films containing donor-π-donor polymers in combination with carefully controlled co-polymers.

Additionally, some metal organic frameworks can be used as electrochromic materials. Alkaabi et al. discloses a naphthalene diimide (NDI)-based metal organic framework which has been shown to undergo transparent to dark optical transitions.

In this case, a black colour was obtained by balancing the amount of radical anion and dianion at a ratio of 1:1. These metal organic frameworks have the drawback that they can be expensive to design and manufacture.

Al Kobaisi et al. reviews the synthesis and the use of naphthalene diimide compounds, including their use in artificial photosynthesis and solar cell technology.

The present invention aims to solve one or more of the above problems.

SUMMARY OF THE INVENTION

In a first aspect, the present invention provides a naphthalene diimide (NDI) compound of Formula 1, and the salts and solvates thereof.

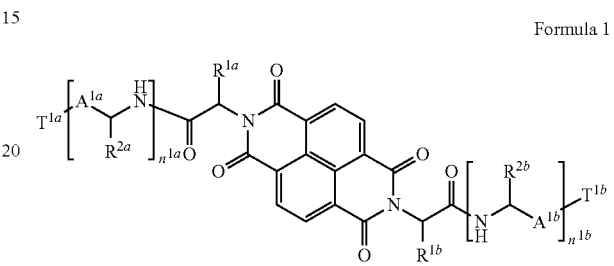

Formula 1

In Formula 1, $R^{1a}$ and $R^{1b}$ may be independently selected from hydrogen, benzyl, phenyl, $C_{1-6}$ alkyl, indolyl and

[C(O)—N(H)—CR'R"]$_m$—X wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

In Formula 1, $R^{2a}$ and $R^{2b}$ may be independently selected from hydrogen, benzyl, phenyl, $C_{1-6}$ alkyl, indolyl and

[C(O)—N(H)—CR'R"]$_m$—X wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, and —NH—C(=NH)—NH$_2$.

In Formula 1, each of -$A^{1a}$- and -$A^{1b}$- may be independently selected from —C(O)—, —C(=NR)—CH$_2$— and a covalent bond where R is hydrogen or $C_{1-6}$ alkyl.

In Formula 1, $T^{1a}$ and $T^{1b}$ may be independently selected from —OH, —NH$_2$, —NHMe, $C_{1-6}$ alkyl, phenyl and benzyl.

In Formula 1, each of $n^{1a}$ and $n^{1b}$ is independently an integer from 0 to 5.

In some embodiments, the naphthalene diimide (NDI) compound of Formula 1 is a compound of Formula 1a, and the salts and solvates thereof.

Formula 1a

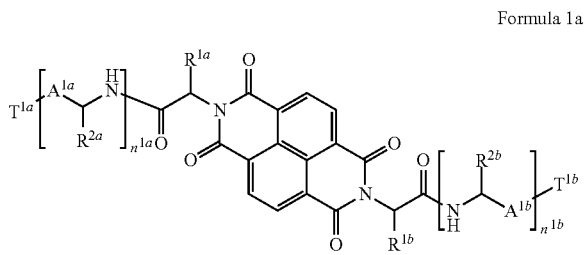

In Formula 1a, $R^{1a}$ and $R^{1b}$ may be independently selected from hydrogen, benzyl, phenyl, $C_{1-6}$ alkyl and indolyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

In Formula 1a, $R^{2a}$ and $R^{2b}$ may be independently selected from hydrogen, benzyl, phenyl, $C_{1-6}$ alkyl and indolyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

In Formula 1a, each of -$A^{1a}$- and -$A^{1b}$- may be independently selected from —C(O)—, —CH$_2$— and a covalent bond.

In Formula 1a, $T^{1a}$ and $T^{1b}$ may be independently selected from —OH, —NH$_2$ and —NHMe.

In Formula 1a, each of $n^{1a}$ and $n^{1b}$ is independently an integer from 1 to 5.

The compound of Formula 1a may have the structure:

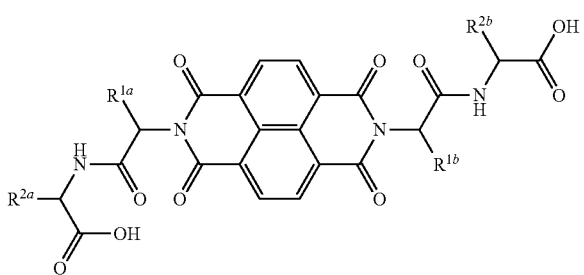

where the groups $R^{1a}$, $R^{1b}$, $R^{2a}$ and $R^{2b}$ have the same meanings as above for Formula 1a.

The compounds of the invention exhibit colour change from substantially transparent to substantially black upon electrochemical or photochemical stimulus. The colour change may be rapid and is reversible over many cycles.

In this way, the present invention provides compound that are useful for photochromic and electrochromic devices, in particular for smart windows.

In a further aspect, the present invention provides a composition comprising an NDI of Formula 1, preferably Formula 1a, and a solvent.

In a further aspect, the present invention provides a gel comprising an NDI of Formula 1, preferably Formula 1a, and a solvent. The gel is obtainable from or obtained by gelation of a composition comprising the NDI of Formula 1, preferably Formula 1a, and the solvent.

Electrochromic devices typically include at least two electrodes and an electrolyte layer. The colour change results from the electrochromic species going from a bleached state (giving rise to the transparent appearance) to the coloured state. Electrochromic devices are classified into three categories. The first is where the coloured and bleached species are both soluble in the electrolyte. The second is where the bleached state is soluble whilst the coloured state coats one of the electrodes. The third case is where both the bleached and coloured species coat an electrode.

In the present invention, the gel matrix itself has been shown to be an effective means of forming transparent-to-black smart windows. It is proposed that neither the bleached nor the coloured state is soluble, nor does either coat an electrode.

Potential advantages include limited diffusion in a system where the matrix is essentially solid, meaning that it should be possible to localise colour changes, and limited migration of species to either electrode, which might lead to degradation of the device with time.

In a further aspect, the present invention provides an electrochemical device comprising two electrodes and a solution or gel of the invention. The solution or the gel is provided in the interelectrode space.

In a further aspect, the present invention provides the use of a solution or gel of the invention in a photo- or electrochromic device.

In another aspect, the present invention provides a method of producing a gel comprising providing a solution comprising a solvent and a naphthalene diimide compound of Formula 1, preferably Formula 1a, and reducing the pH of the solution, thereby to form the gel.

These and other aspects and embodiments of the invention are described in further detail below.

DETAILED DESCRIPTION OF THE INVENTION

Compounds

Figure 1:
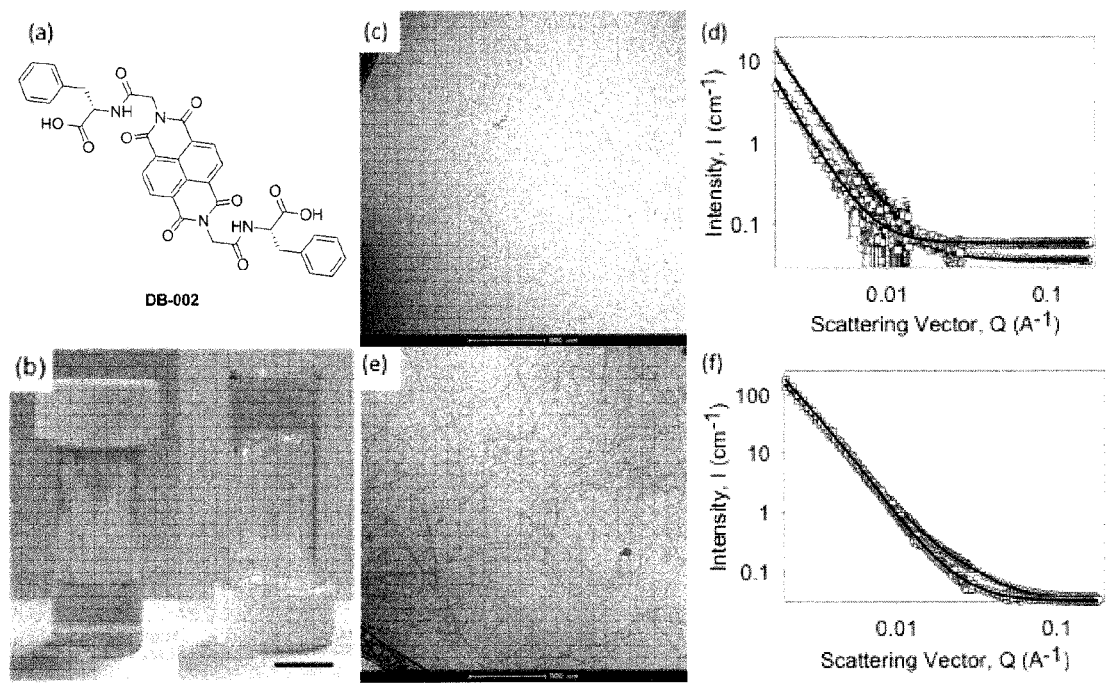
FIG. 1 shows (a) Chemical structure of 1; (b) Photograph of (left) a solution and (right) a gel of 1 in water/glycerol (80/20); (c) cryo-TEM of a solution of 1 in water/glycerol; (d) SANS data for a solution of 1 in water/glycerol (80/20). The lower intensity line (at 0 cm$^{-1}$) relates to the sample as prepared, the upper intensity line (at 0 cm$^{-1}$) relates to the sample after irradiation with a 365 nm LED for 5 minutes, with the lower intensity line also including data for an irradiated sample that was subsequently allowed to relax for 8 hours (thus the lower intensity line includes an overlay of the prepared sample data and the irradiated and relaxed sample data); (e) cryo-TEM for a gel of 1 in water/glycerol (80/20); (d) SANS data for a gel of 1 in water/glycerol (80/20). The lower intensity line (at ca. 0.07 cm$^{-1}$) relates to the sample as prepared, the upper intensity line (at ca. 0.07 cm$^{-1}$) relates to the sample after irradiation with a 365 nm LED for 5 minutes, with the lower intensity line also including data for an irradiated sample that was subsequently allowed to relax for 8 hours (thus the lower intensity line includes an overlay of the prepared sample data and the irradiated and relaxed sample data).

The present invention provides a naphthalene diimide (NDI) compound of formula 1, and the salts and solvates thereof.

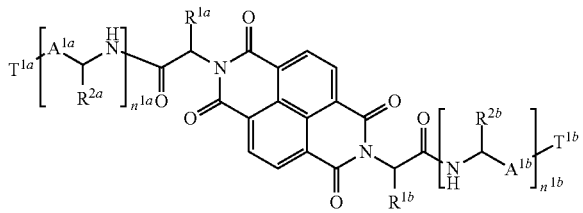

Formula 1

In Formula 1, $R^{1a}$ and $R^{1b}$ may be independently selected from hydrogen, benzyl, phenyl, $C_{1-6}$ alkyl, indolyl and

[C(O)—N(H)—CR'R"]$_m$—X wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

In Formula 1, $R^{2a}$ and $R^{2b}$ may be independently selected from hydrogen, benzyl, phenyl, $C_{1-6}$ alkyl, indolyl and

[C(O)—N(H)—CR'R"]$_m$—X wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, and —NH—C(=NH)—NH$_2$.

In Formula 1, each of -$A^{1a}$- and -$A^{1b}$- may be independently selected from —C(O)—, —C(=NR)—CH$_2$— and a covalent bond where R is hydrogen or $C_{1-6}$ alkyl.

In Formula 1, $T^{1a}$ and $T^{1b}$ may be independently selected from —OH, —NH$_2$, —NHMe, $C_{1-6}$ alkyl, phenyl and benzyl.

In Formula 1, each of $n^{1a}$ and $n^{1b}$ is independently an integer from 0 to 5.

Preferably, the naphthalene diimide (NDI) compound of Formula 1 is a compound of Formula 1a, and the salts and solvates thereof.

Formula 1a

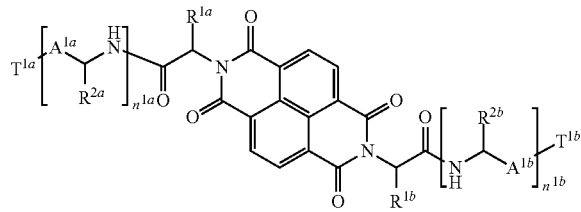

$R^{1a}$ and $R^{1b}$ may be independently selected from hydrogen, benzyl, phenyl, $C_{1-6}$ alkyl and indolyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

$R^{1a}$ and $R^{1b}$ may be independently selected from hydrogen, benzyl and $C_{1-6}$ alkyl, where the benzyl and $C_{1-6}$ alkyl may be substituted as before.

In some cases $R^{1a}$ and $R^{1b}$ are the same. Preferably, $R^{1a}$ and $R^{1b}$ are hydrogen.

$R^{2a}$ and $R^{2b}$ may be independently selected from hydrogen, benzyl, phenyl, $C_{1-6}$ alkyl and indolyl wherein the benzyl, phenyl, $C_{1-6}$ alkyl and indolyl may be optionally substituted with one or more groups selected from —OH, —F, —Cl, —Br, —F, —SH, —SeH, —COOH, —NH$_2$, or —NH—C(=NH)—NH$_2$.

In some cases $R^{2a}$ and $R^{2b}$ are the same. Preferably, $R^{2a}$ and $R^{2b}$ are benzyl.

Where an alkyl group is present, for example at one or more of $R^{1a}$, $R^{1b}$, $R^{2a}$ or $R^{2b}$, this may be a linear or branched alkyl group.

A $C_{1-6}$ alkyl group may be $C_{1-5}$ alkyl, such as $C_5$ alkyl.

Each of $n^{1a}$ and $n^{2a}$ is an integer from 1 to 5, such as 1 to 3, such as 1 or 2. Where $n^{1a}$ and/or $n^{1b}$ is greater than 1, the sequence of contiguous units (set out in the square brackets) may be referred to as an oligomer, and where -$A^{1a}$- and/or -$A^{1b}$- is —C(O)— the repeat units may be referred to as peptides, such as trimers, when $n^{1a}$ and $n^{2a}$ are 2 (together with the preceding amino acid residue containing the group $R^{1a}$ a or $R^{1b}$).

Preferably each of $n^{1a}$ and $n^{2a}$ is 1.

Alternatively, one or both of $n^{1a}$ and $n^{2a}$ is 2.

Each of -$A^{1a}$- and -$A^{1b}$- may be independently selected from —C(O)—, —CH$_2$— and a covalent bond. As noted above, where -$A^{1a}$- and -$A^{1b}$- are —C(O)— the repeat unit is an amino acid residue. Where -$A^{1a}$- and -$A^{1b}$- are —CH$_2$— or a covalent bond the repeat unit may be regarded as an amino acid residue mimetic.

Preferably each of -$A^{1a}$- and -$A^{1b}$- is —C(O)—.

Where $n^{1a}$ and/or $n^{1b}$ is greater than 1, each repeat unit may have the same or different substituents at $R^{2a}$, $R^{2b}$, -$A^{1a}$- and $A^{1b}$-.

The sequence of contiguous units has a terminal unit which is the group in the sequence where -$A^{1a}$- and -$A^{1b}$- is directly connected to the terminal group $T^{1a}$ and $T^{1b}$ respectively. In this terminal group, each of -$A^{1a}$- and -$A^{1b}$- may be selected from —C(O)—, —CH$_2$— and a covalent bond. Where there are other units within the sequence these units preferably have groups -$A^{1a}$- and -$A^{1b}$- that are each —C(O)—. Thus, a peptide sequence is maintained in the sequence of contiguous units, except at the C terminal, which may contain alternative functionality, such as an amine functionality or a hydroxyl functionality.

$T^{1a}$ and $T^{1b}$ may be independently selected from —OH, —NH$_2$ and —NHMe. Preferably, $T^{1a}$ and $T^{1b}$ are each —OH, and most preferably together with the groups -$A^{1a}$- and -$A^{1b}$- to which they are directly connected (for example, within the terminal group), which are preferably each —C(O)—, form terminal carboxylic acids.

Each of $T^{1a}$ and $T^{1b}$ may be —NH$_2$ or —NHMe when the groups -$A^{1a}$- and -$A^{1b}$- to which they are directly connected are —C(O)—, thereby forming terminal carboxamides.

NDIs are known to be easily reduced to the radical anion and dianion. The radical anions may be chromophores that absorb in the visible and near-infrared.

In the solid state, photochromic formation of the NDI radical anion has been shown to result in changes from yellow to black, as long as the interplanar distance between NDI molecules is small, allowing effective π-electron delocalization.

The NDI compounds of the present invention have the ability to switch from a substantially transparent to substantially black colour upon photochemical or electrochemical stimulus in solution or in a gel. The electrochemical stimulus requires a low potential. The NDI compounds of the invention show good cyclability, good temperature stability and good response speeds.

The ability to change colour in response to both photo- and electro-chemical stimulus provides additional advantages. For example, if the compounds of the invention are used in smart windows, the photochromic darkening of the window reduces transmittance without the need for any energy input. Low voltages can be applied if a transparent window is desired.

In this way, the present invention provides compounds with colour change properties that may be commercial useful, for example, which may be useful in smart windows.

In some cases, the compound of Formula 1a has the structure:

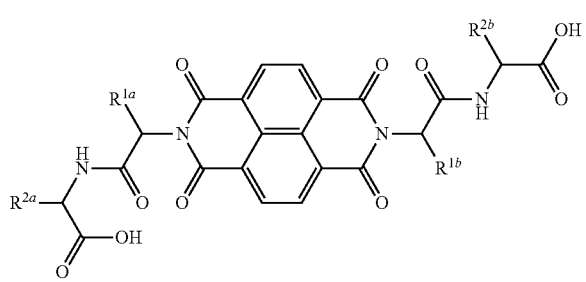

This is a compound where each of $n^{1a}$ and $n^{1b}$ is 1, each of -$A^{1a}$- and -$A^{1b}$- is —C(O)—, and each of $T^{1a}$ and $T^{1b}$ is —OH. The groups $R^{1a}$, $R^{2a}$ and $R^{2b}$ have the same meanings as before for Formula 1a.

In some cases, the compound of Formula 1a is a compound of Formula 1aa:

Formula 1aa

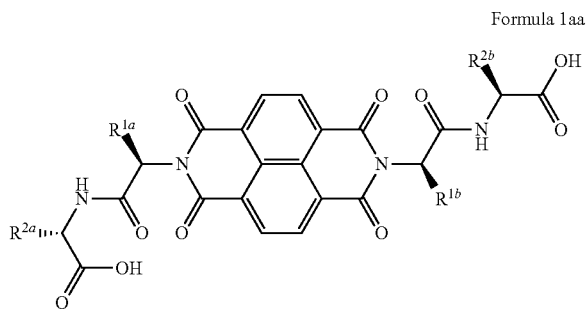

Examples of compounds of Formula 1a include:

Compound 1

Compound 1a

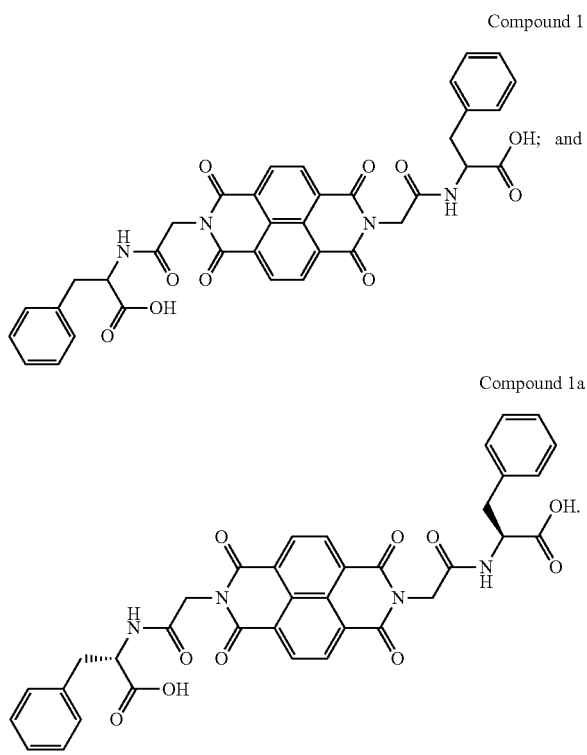

The compounds of the invention may also be provided as solvates or salts, where appropriate.

The solvate may be a hydrate.

The compound may be provided in salt form, for example where carboxylic acid or amino functionality is provided. The salt may be the additional salt of the carboxylic acid or the amine.

The compounds of Formula 1, such as compounds of Formula 1a, are readily obtainable using standard synthetic methods, as exemplified in the worked examples of the present case. Typically the central core of the NDI is derived from naphthalene-1,4,5,8-tetracarboxylic acid dianhydride. This dianhydride may be reacted with suitable amino acid-functionalized reagents to generate the naphthalene diimide form with pendant amino acid-bearing arms.

General methods for the preparation of NDI compounds are also well known in the art, for examples as reviewed by Al Kobaisi et al.

Unless specified, the compounds of the invention may exist in one or more or more particular optical, enantiomeric, or diasteriomeric forms, hereinafter collectively referred to as "isomers" (or "isomeric forms").

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

Solutions

In a further aspect, the present invention provides a composition comprising an NDI of Formula 1, preferably Formula 1a, and a solvent. The composition of the invention is less preferred over the gel of the invention, as the gel exhibits reduced colour bleeding, owing to reduced diffusion.

The NDI of Formula 1 and Formula 1a is as discussed above.

The solvent may be any suitable solvent. In some embodiments, the solvent is selected from water, glycerol or mixtures thereof. Preferably, the solvent is a mixture of water and glycerol.

In some cases, the water:glycerol mixture ratio is from 50:50 to 90:10

In some cases, the concentration of the NDI of Formula 1, preferably Formula 1a, in the composition is at least 0.4 mg/mL, at least 0.5 mg/mL or at least 0.6 mg/mL.

In some cases, the concentration of the NDI of formula 1, preferably Formula 1a, in the composition is at most 20 mg/mL, at most 15 mg/mL, at most 10 mg/mL, at most 6 mg/mL or at most 3 mg/mL.

The NDI of formula 1, preferably Formula 1a, may be present in an amount in a range with the lower and upper amounts selected from the values given above. For example, the NDI of formula 1, preferably Formula 1a, may be present in an amount in the range 0.5 to 10 mg/mL.

In some cases the pH of the composition may be from 6 to 10, for example from 7 to 9. The pH of the composition may be measured using a Hanna Edge FC2020 pH probe with a given error of ±0.1. The pH may be measured at ambient temperature, such as 20° C., The composition may further comprise an electrolyte. The electrolyte may be selected from any suitable electrolyte, for example the electrolyte may be sodium chloride.

In some cases, the concentration of the electrolyte in the composition is at least 0.01 M, at least 0.05 M or at least 0.1 M.

In some cases, the concentration of the electrolyte in the composition is at most 10 M, at most 1 M, at most 0.5 M or at most 0.3 M.

The electrolyte may be present in an amount in a range with the lower and upper amounts selected from the values given above. For example, the electrolyte may be present in an amount in the range 0.05 to 0.3 M.

The composition may further comprise a solubilizing agent. The solubilizing agent may be selected from any suitable solubilizing agent, for examples the solubilizing agent may be sodium hydroxide.

Gels

In a further aspect, the present invention provides a gel comprising an NDI of formula 1, preferably Formula 1a, and a solvent.

The NDI of Formula 1 and Formula 1a is as discussed above.

A number of NDIs have been shown to be effective low molecular weight gelators, small molecules that can self-assemble into a fibrous network that can immobilise a solvent.

An electrochromic NDI based gel has been previously reported and shown to absorb in the near infra-red on reduction to the radical anion (see Zhang et. al.).

Gels provide additional advantages compared to, for example, solutions. Gels have reduced leakage for example, if a device containing the gel is broken.

The gels of the present invention exhibit reduced diffusion. In this way, the gels allow patterning to be applied and maintained during black-to-transparent transitions.

In some cases, the gel may be a hydrogel.

The solvent may be any suitable solvent. In some embodiments, the solvent is selected from water, glycerol or mixtures thereof. Preferably, the solvent is a mixture of water and glycerol. The water and glycerol may be present at any suitable relative amounts.

In some cases, the water:glycerol mixture ratio (volume ratio) is from 1:99 to 90:10, 10:90 to 90:10, for example from 50:50 to 90:10, for example from 60:40 to 90:10, or from 75:25 to 85:15.

In some cases, the concentration of the NDI of formula 1, preferably Formula 1a, in the gel is at least 0.40 mg/mL, at least 0.45 mg/mL, at least 0.50 mg/mL, at least 0.55 mg/mL, at least 0.60 mg/mL, at least 0.65 mg/mL.

In some cases, the concentration of the NDI of formula 1, preferably Formula 1a, in the gel is at most 20 mg/mL, at most 15 mg/mL, at most 10 mg/mL, at most 6 mg/mL or at most 3 mg/mL.

The NDI of Formula 1, preferably Formula 1a, may be present in an amount in a range with the lower and upper amounts selected from the values given above. For example, the NDI of Formula 1, preferably Formula 1a, may be present in an amount in the range 0.5 to 10 mg/mL.

A gel may be formed from a solution of the invention, for example by gelation of the solution. The gel may be formed by changing the pH of a composition containing the NDI and the solvent, for example by decreasing the pH.

In some cases the pH of the gel is from 2 to 7, preferably from 2 to 4. The pH of the mixture may be measured using a Hanna Edge FC2020 pH probe with a given error of ±0.1. The pH may be measured at ambient temperature, such as 20° C., The gel may further comprise an electrolyte. The electrolyte may be selected from any suitable electrolyte, for example the electrolyte may be sodium chloride.

In some cases, the concentration of the electrolyte in the gel is at least 0.01 M, at least 0.05 M or at least 0.1 M.

In some cases, the concentration of the electrolyte in the gel is at most 10 M, at most 1 M, at most 0.5 M or at most 0.3 M.

The electrolyte may be present in an amount in a range with the lower and upper amounts selected from the values given above. For example, the electrolyte may be present in an amount in the range 0.05 to 0.3 M.

In some cases, the gel may further comprise an acidifying agent. The acidifying agent may be selected from any suitable acidifying agent, for example the acidifying agent may be glucono-δ-lactone (GdL).

The acidifying agent may be referred to as a gelation initiator owing to its ability to trigger the formation of the gel from a solution of the gel in a solvent. Other agents that are capable of initiating gelation may be used in place of an acidifying agent, such as the glucono-δ-lactone exemplified in the worked examples of the present case. For example, a base-triggered gel may use a basic agent to initiate gelation.

In some cases, the concentration of the acidifying agent in the gel is at least 1 mg/mL, at least 2 mg/mL, at least 4 mg/mL or at least 5 mg/mL.

In some cases, the concentration of the acidifying agent in the gel is at most 20 mg/mL, at most 15 mg/mL, at most 10 mg/mL, at most 8 mg/mL or at most 6 mg/mL.

The acidifying agent may be present in an amount in a range with the lower and upper amounts selected from the values given above. For example, the acidifying agent may be present in an amount in the range 0.5 to 10 mg/mL.

The composition for forming the gel may further comprise a solubilizing agent. The solubilizing agent may be selected from any suitable solubilizing agent, for examples the solubilizing agent may be sodium hydroxide.

The gel may comprise a fibrous network of the NDI of Formula 1, preferably Formula 1a. This is in contrast to the solutions described above, where little or no structure is observed. The presence (or not) of a fibrous network may be determined by analysis of gels and solutions by SANS and TEM, including cryo-TEM.

These spectroscopic techniques show that changes in the gel colour are advantageously not associated with any degradation in the gel structure. These techniques do show that the structure of the gel is slightly affected by irradiation, together with the associated colour change, however this slight change does not lead to the gel losing its structural integrity, and the gel recovers its structure when the colour change is reverted.

The gel may have a storage and loss modulus that is typically of low weight molecular gels. The storage and loss modulus may be substantially unchanged when the gel is subjected to photochemical or electrochemical stimulus. That is, the storage and loss modulus remain at similar values in the transparent and black states of the gel.

The storage modulus value (G') of a gel may be the value recorded at 25° C. from a strain amplitude sweep measurement and is the value taken at a strain value in the range 0.1 to 1,000%, for example 0.01 to 100%. The angular frequency may be 10 or 60 rad/s, such as 10 rad/s.

In one embodiment, the gel has a storage modulus, G', (from a strain amplitude sweep measurement) of at least 10 Pa, at least 100 Pa, at least 1,000 Pa, at least 2,000 Pa, or at least 5,000 Pa.

In one embodiment, the gel has a storage modulus, G', (from a strain amplitude sweep measurement) of at most 5,000 at most 10,000 Pa, at most 50,000 Pa, at most 100,000 Pa, or at most 200,000 Pa.

In one embodiment, the gel has a storage modulus (from a strain amplitude sweep measurement) in a range where the minimum and maximum amounts are selected from the embodiments above. For example, the storage modulus is in the range 100 to 10,000 Pa.

Alternatively, the storage modulus value of the gel may be the value recorded at 25° C. from a frequency sweep measurement and is the value taken at a frequency value in the range 1 to 100 rad/s. The strain may be 0.5% or 1%, preferably 0.5%.

In one embodiment, the gel has a storage modulus (from a frequency sweep measurement) of at least 100 Pa, at least 500 Pa, at least 1,000 Pa, at least 2,000 Pa, or at least 4,000 Pa.

In one embodiment, the gel has a storage modulus (from a frequency sweep measurement) of at most 10,000 Pa, at most 15,000 Pa, at most 50,000 Pa, at most 100,000 Pa or at most 200,000 Pa.

In one embodiment, the gel has a storage modulus (from a frequency sweep measurement) in a range where the minimum and maximum amounts are selected from the embodiments above. For example, the storage modulus is in the range 10 to 10,000 Pa, for example 100 to 10,000 Pa, such as 1,000 to 10,000 Pa.

The loss modulus value (G") of the gel may be the value recorded at 25° C. from a strain amplitude sweep measurement and is the value taken at a strain value in the range 0.1 to 1000%, for example 0.01 to 100%. The angular frequency may be 10 or 60 rad/s, such as 10 rad/s.

In one embodiment, the gel has a loss modulus (from a strain amplitude sweep measurement) of at least 1 Pa, at least 10 Pa, at least 100 Pa, or at least 300 Pa.

In one embodiment, the gel has a loss modulus (from a strain amplitude sweep measurement) of at most 1,000 Pa, at most 2,000 Pa, at most 5,000 Pa, or at most 10,000 Pa.

In one embodiment, the gel has a loss modulus (from a strain amplitude sweep measurement) in a range where the minimum and maximum amounts are selected from the embodiments above. For example, the loss modulus is in the range 100 to 1,000 Pa, for example 300 to 1,000 Pa.

Alternatively, the loss modulus value of the gel may be the value recorded at 25° C. from a frequency sweep measurement and is the value taken at a frequency value in the range 1 to 100 rad/s. The strain may be 0.5% or 1%, preferably 0.5%.

In one embodiment, the gel has a loss modulus (from a frequency sweep measurement) of at least 1 Pa, at least 10 Pa, at least 100 Pa, at least 300 Pa, or at least 500 Pa. In one embodiment, the gel has a loss modulus (from a frequency sweep measurement) of at most 800 Pa, at most 900 Pa, at most 1,000 Pa, or at most 10,000 Pa.

In one embodiment, the gel has a loss modulus (from a frequency sweep measurement) in a range where the minimum and maximum amounts are selected from the embodiments above. For example, the loss modulus is in the range 1 to 800 Pa, for example 10 to 900 Pa or from 100 to 1,000 Pa.

The gels of the present case are capable of retaining their storage and loss modulus values over cycles of reduction and oxidation without noticeable loss of modulus.

Thus, the storage and/or loss modulus value for a gel after a strain and self-repair cycle may be at least 90%, at least 95% or at least 98% the value of the gel before the strain.

The strain experiment maybe conducted between the strain of 0.1% and 1,000% at 10 rad $s^{-1}$.

In one embodiment, a rheological property of the gel remains substantially the same following at least one cycle of reduction and oxidation. The rheological property may be one or more properties selected from the group consisting of storage modules and loss modulus.

Methods and Uses

The compounds of Formula 1 and Formula 1a may be synthesized by any suitable method. For example, the compounds of Formula 1 and Formula 1a may be synthesized by coupling a diamide (e.g. a dipeptide) to naphthalene-1,4,5,8-tetracarboxylic acid.

In a further aspect, the present invention provides an electrochemical device comprising two electrodes and a solution or gel of the invention.

In a further aspect, the present invention provides the use of solution of gel of the invention in a photo- or electrochromic device.

In another aspect, the present invention provides a method of producing a gel comprising providing a solution comprising a solvent and a naphthalene diimide compound of Formula 1, preferably Formula 1a, and reducing the pH of the solution. In some cases the pH may be reduced to less than 5, for example less than 4.

In some cases, the pH may be reduced using an acidifying agent. The acidifying agent may be glucono-δ-lactone (GdL).

In some cases, the concentration of the acidifying agent in the solution is at least 1 mg/mL, at least 2 mg/mL, at least 4 mg/mL or at least 5 mg/mL.

In some cases, the concentration of the acidifying agent in the solution is at most 20 mg/mL, at most 15 mg/mL, at most 10 mg/mL, at most 8 mg/mL or at most 6 mg/mL.

The acidifying agent may be present in an amount in a range with the lower and upper amounts selected from the values given above. For example, the acidifying agent may be present in an amount in the range 0.5 to 10 mg/mL.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results

Gelator Synthesis

Compound 1 was synthesised in the reaction between naphthalene-1,4,5,8-tetracarboxylic acid dianhydride and glycine-phenylalanine in molten imidazole following standard protocols.

The compound 1 was synthesised following the steps below. All chemicals and solvent were purchased from Sigma-Aldrich or Alfa Aesar and used as received. Deionised water was used throughout.

Tert-butyl (2S)-2-(2-{[(tert-butoxy)carbonyl]amino}acetamido)-3-phenylpropanoate (DE-007)

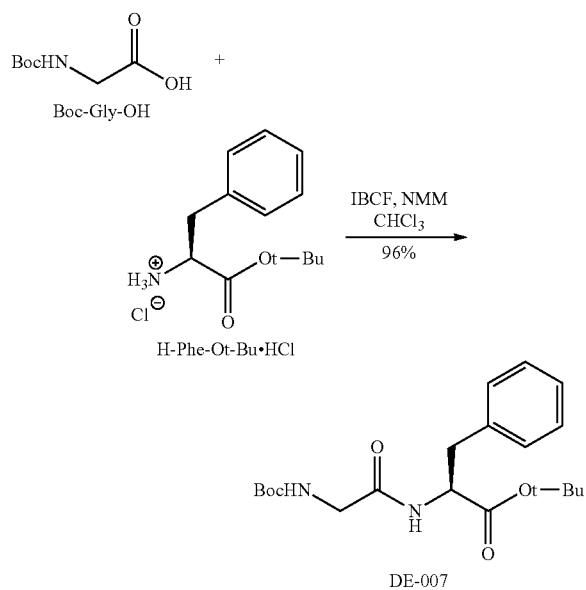

To a solution of Boc-glycine (3.75 g, 21.4 mmol) in chloroform (125 mL) was added N-methylmorpholine (1 eq., 2.35 mL), followed by isobutyl chloroformate (1 eq., 2.78 mL) and the mixture was stirred at ambient temperature for 20 minutes. After this time, L-phenylalanine tert-butyl ester hydrochloride (1 eq., 5.52 g), and another portion of N-methylmorpholine (1 eq., 2.35 mL) were added and the reaction mixture was stirred overnight. It was then diluted with chloroform, washed in turn with water, 1M hydrochloric acid, saturated sodium carbonate solution, and brine, dried (MgSO$_4$), and evaporated to dryness under reduced pressure. The title compound was thus obtained as a pale yellow, viscous oil (7.76 g, 96%) in adequate purity for the next step. A small amount was purified via column chromatography (1:9 ethyl acetate/dichloromethane) to yield an analytical sample.

$\delta_H$ (400 MHz, DMSO-d$_6$) 8.05 (1H, d, J 7.72, CHN$\underline{H}$), 7.30-7.20 (5H, m, $\underline{H}_{Ar}$), 6.93 (1H, t, J 6.04, BocN$\underline{H}$), 4.36 (1H, q, J 7.32, C$\underline{H}$*), 3.53 (2H, dd, J 6.00, 2.32, NHC$\underline{H}_2$), 2.97-2.87 (2H, m, PhC$\underline{H}_2$), 1.37 (9H, s, C(C$\underline{H}_3$)$_3$), 1.31 (9H, s, C(C$\underline{H}_3$)$_3$). $\delta_C$ (100 MHz, DMSO-d$_6$) 170.42, 169.26, and 155.70 ($\underline{C}$=O), 137.02, 129.17, 128.13, and 126.47 ($\underline{C}_{Ar}$), 80.73 and 77.96 ($\underline{C}$(CH$_3$)$_3$), 53.94 ($\underline{C}$H*), 42.91 (NH$\underline{C}$H$_2$), 37.07 (Ph$\underline{C}$H$_2$), 28.14 and 27.47 (C($\underline{C}$H$_3$)$_3$). HRMS (ESI) m/z: [M+Na]$^+$ calcd for C$_{20}$H$_{30}$N$_2$NaO$_5$ 401.2047; found 401.2031.

(2S)-2-(2-Aminoacetamido)-3-phenylpropanoic acid trifluoroacetate (DF-002)

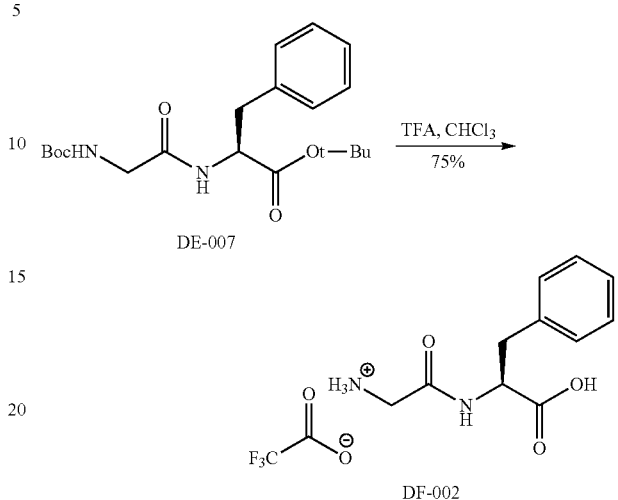

To a solution of DE-007 (7.74 g, 20.4 mmol) in chloroform (50 mL) was added trifluoroacetic acid (6 eq., ca. 9.5 mL) and the mixture was stirred overnight. After this time, TLC (1:9 ethyl acetate/dichloromethane) still indicated the presence of starting material. Another portion of trifluoroacetic acid (10 mL) was added and stirring continued overnight. After this time, the reaction had gone to completion, as judged by TLC. It was poured into diethyl ether (500 mL) and stirred for 30 minutes. The solids were filtered off, washed with diethyl ether in the filter and dried under vacuum overnight. The title compound was thus obtained as a white solid (5.15 g, 75%) and not purified any further.

$\delta_H$ (400 MHz, DMSO-d$_6$) 13.07 (1H, br s, COO$\underline{H}$), 8.74 (1H, d, J 7.96, NH), 7.98 (3H, br s, N$\underline{H}_3^+$), 7.31-7.20 (5H, m, $\underline{H}_{Ar}$), 4.54-4.48 (1H, m, C$\underline{H}$*), 3.58 (1H, d, J 16.40, $\underline{H}_a$H$_b$C—NH$_3^+$), 3.48 (1H, d, J 16.28, H$_a\underline{H}_b$C—NH$_3^+$), 3.10 (1H, dd, J 13.86, 4.74, PhC$\underline{H}_a$H$_b$), 2.88 (1H, dd, J 13.78, 9.06, PhCH$_a\underline{H}_b$). $\delta_C$ (100 MHz, DMSO-d$_6$) 172.46 and 166.00 ($\underline{C}$=O), 158.43 (q, J 31.26, F$_3$C—$\underline{C}$=O), 137.31, 129.22, 128.35, and 126.65 ($\underline{C}_{Ar}$), 117.26 (q, J 299.39, $\underline{C}$F$_3$), 53.84 ($\underline{C}$H*), 40.05 (H$_2\underline{C}$—NH$_3^+$), 36.84 (Ph$\underline{C}$H$_2$). HRMS (ESI) m/z: [M]$^+$ calcd for C$_{11}$H$_{15}$N$_2$O$_3$ 223.1077; found 223.1083.

2-[2-[13-{[(1-Carboxy-2-phenylethyl)carbamoyl]methyl}-5,7,12,14-tetraoxo-6,13-diazatetracyclo[6.6.2.0$^{4,16}$.0$^{11,15}$]hexadeca-1,3,8(16),9,11(15)-pentaen-6-yl)acetamido]-3-phenylpropanoic Acid (NDI-GF, DB-002)

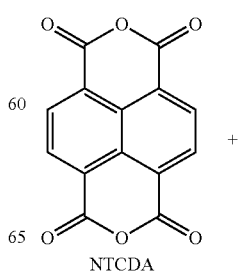

NTCDA

+

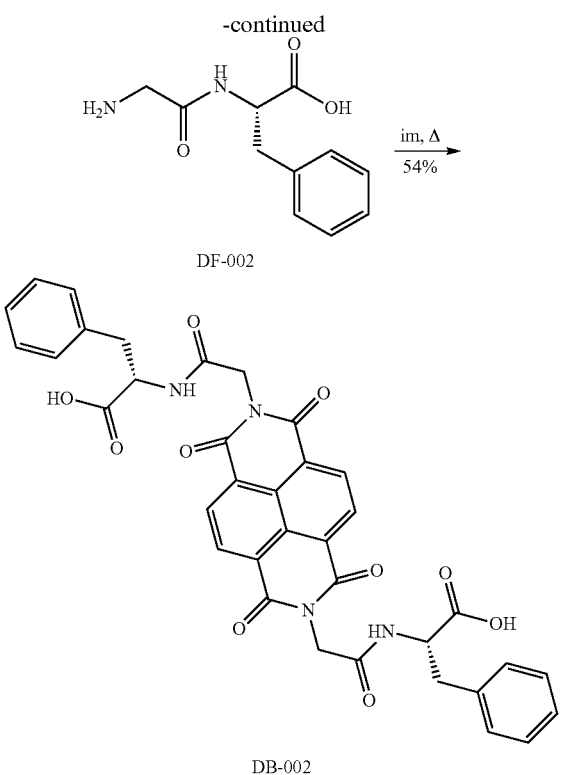

DF-002

DB-002

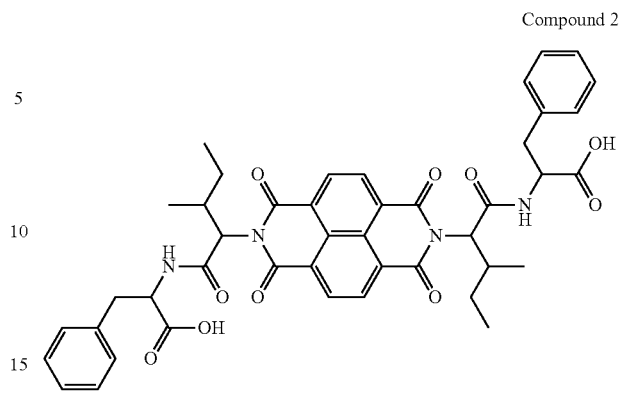

Compound 2

¹H NMR (500 MHz, ppm, DMSO-d₆) 0.75 (3H, d, J=6.75 Hz, Me*CH (Ile)), 0.79 (3H, t, J=7.38 Hz, MeCH₂*CH), 0.85 (2H, m, MeCH₂*CH), 1.04 (1H, m, Me*CHCH₂), 1.31 (9H, s, O^tBu), 1.38 (9H, s, O^tBu), 2.94 (2H, m, CH₂ (Phe)), 3.84 (1H, t, J=8.40 Hz, *CH (Phe)), 4.39 (1H, dd, J=7.45, 14.85 Hz, *CH (Ile)), 6.61 (1H, d, J=9.20 Hz, NH (Ile)), 7.18-7.30 (5H, m, Ph ring), 8.15 (1H, d, J=7.55 Hz, NH (Phe)).

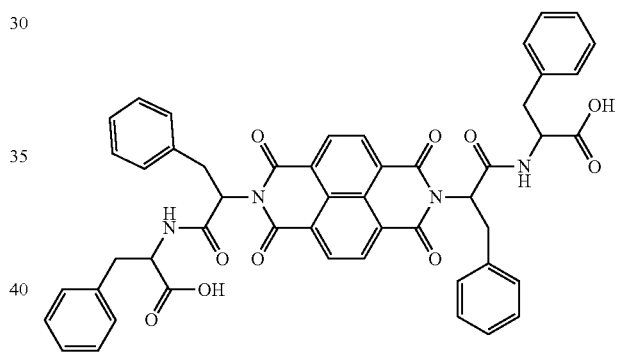

Compound 3

Naphthalene-1,4,5,8-tetracarboxylic acid dianhydride (NTCDA, 1.98 g, 7.37 mmol), DF-002 (2 eq, 4.95 g), and imidazole (30 eq, 15 g) were mixed intimately and stirred at 120° C. in a Schlenk tube under an argon atmosphere for 5 hours. The temperature was then reduced to 90° C., water (ca. 50 mL) was added and stirring continued at 90° C. for a further hour, after which the mixture was allowed to cool to ambient temperature overnight. Insoluble materials were filtered off and the filtrate was poured into dilute hydrochloric acid (1 M, ca. 300 mL), and stirred for 30 minutes. The precipitate was filtered off, washed with water, and transferred into another 300 mL portion of 1M hydrochloric acid, where it was heated at 90° C. with stirring overnight. The solids were filtered off, washed with water, and dried by azeotropic distillation with acetonitrile. The title compound DB-002 (compound 1) was thus obtained as a dark-gray solid (2.67 g, 54%) in 98.5% purity by NMR (balance: acetonitrile). Further removal of acetonitrile may be accomplished by heating to 90° C. under vacuum.

$\delta_H$ (400 MHz, DMSO-d₆) 12.79 (2H, br s, COOH), 8.72 (4H, s, NDI-$H_{Ar}$), 8.64 (2H, d, J 7.88, NH), 7.32-7.22 (10H, m, C₆H₅), 4.72 (2H, d, J 16.44, NCH$_a$H$_b$), 4.68 (2H, d, J 16.48, NCH$_a$H$_b$), 4.44 (2H, dt, J 5.30, 8.23, CH*), 3.04 (2H, dd, J 5.12, 13.64, PhCH$_a$H$_b$), 2.90 (2H, dd, J 13.70, 8.66, PhCH$_a$H$_b$). $\delta_C$ (100 MHz, DMSO-d₆) 172.64, 166.29, and 162.28 (C=O), 137.36, 130.75, 129.25, 128.24, 126.52, 126.20, and 126.17 ($C_{Ar}$), 53.78 (CH*), 42.50 (NCH₂), 36.79 (PhCH₂). HRMS (FAB, nitrobenzyl alcohol matrix) m/z: [M+H]⁺ calcd for C₃₆H₂₉N₄O₁₀ 677.1884; found 677.1870.

Additional compounds 2, and 3 were synthesized in a manner analogous to compound 1.

¹H NMR (500 MHz, ppm, DMSO-d₆) 2.7-2.9 (4H, m, NH—*CH—CH₂), 3.0-3.3 (2H, m, (CO)₂N—*CH—CH$_a$H$_b$), 3.6 (2H, m, (CO)₂N—*CH—CH$_a$H$_b$), 4.4 (2H, m, *CH), 5.6 (2H, m, *CH), 6.9-7.0 (20H, m, Ph rings), 8.3-8.7 (6H, m, Ar CH (core) and NH), 12.68 (2H, bs, COOH). ¹³C NMR (100 MHz, ppm, DMSO-d₆): 36.62 (CH₂), 37.13 (CH₂), 54.59 (*CH), 55.65 (*CH), 128.41-128.89 (Ar CH (core)), 129.35-129.66 (Ph ring), 160.16 (COOH), 173.07 (CO), 173.64-174.69 (CO (Core)).

Formation of Solutions and Gels

Solutions were prepared at a concentration of 2.5 mg/mL of gelator (compound 1). The gelator was dissolved in 2 molar equivalents of NaOH (aqueous), this was then made up to the desired volume using an 80/20 water/glycerol mixture. A background electrolyte of NaCl was used at a concentration of 0.1 M.

To prepare the gels, the solution as described above was added to 5 mg/mL of glucono-δ-lactone (GdL) in a vial. The solution was gently shaken until the GdL had dissolved and then transferred to the sample container, cuvette, mould, or device where it was allowed to gel. The samples were left overnight to gel. For rheology and photographs they were prepared in 7 mL Sterilin vials. Gels for UV-vis absorption and SANS measurements were prepared in 2 mm pathlength quartz cuvettes. For the chromic windows, the solutions were injected into the FTO cells, as described below.

Rheology Measurements

All rheological measurements were performed using an Anton Paar Physica 301 rheometer, fitted with a chiller for cold temperature measurements. Temperature calibrations were performed between −30 and 80° C. before starting the temperature measurements to ensure the correct temperature was being recorded.

All data were collected using a vane (ST10-4V-8.8/97.5) and cup geometry (H-24-D) so samples could be prepared in aluminium cups or Sterlin vials to reduce problems with loading issues.

There was a gap distance of 1.5 mm between the bottom of the gel and the cup. A zero force of 0 N was maintained throughout the experiments. Measurements were recorded in triplicate. All measurements were recorded in the linear viscoelastic region of the gels as determined by the strain sweeps, which are recorded first. G' and G" are determined from the frequency sweeps at 10 rad/s. The yield point is determined at the point at where G' and G" deviate from linearity in the strain sweep, and the flow point where G" crosses over G'.

Strain Sweeps: Strain sweeps were recorded from 0.1-1000% strain at 10 rad/s. They were recorded at 25° C. in triplicate. Gel samples of 2 mL were prepared in 7 mL Strelin vials as previously described.

Frequency Sweeps: Frequency sweeps were recorded from 1-100 rad/s at a strain of 0.5%. They were recorded at 25° C. in triplicate. Gel samples of 2 mL were prepared in 7 mL Strelin vials, as previously described.

Temperature dependence Measurements: G' and G" were recorded over time at a frequency of 10 rad/s and a strain of 0.5%. The temperature was then lowered at a rate of 0.5° C./min from 45° C. to −10° C. To ensure the correct sample temperature a Eurotherm type K thermocouple was also used. Samples were measured in triplicate and prepared in aluminium cups as previously described.

SANS

SANS measurements were performed using the D33 instrument (Institut Laue Langevin, Grenoble, France). A neutron beam, with a divergence of $\Delta\lambda/\lambda=10.2\%$, allowed measurements over a Q-range range of 0.002 to 0.18 Å$^{-1}$ using three sample-detector distances; for low Q data, a wavelength of 13 Å with the detector at 12.5 m; for middle Q data, 6 Å with the detector at 12.5 m; for high Q data, 6 Å and a 2 m detector distance. The data were fitted using Sasview, as described by Doucet et al.

Cryo-TEM

Cryogenic TEM imaging was performed using a FEI Tecnai 12 TWIN Transmission Electron Microscope, operating at 100 kV. The TEM grids were treated with plasma air to render the lacey carbon film hydrophilic. A thin film of the sample solution was produced using the Vitrobot with a controlled humidity chamber (FEI). After loading of the sample solution, the lacey carbon grid was blotted using pre-set parameters and plunged instantly into a liquid ethane reservoir precooled by liquid nitrogen. The vitrified samples were transferred to a cryo-holder using a cryo-transfer stage which was cooled by liquid nitrogen. The cryo-holder temperature was maintained below −170° C. during the imaging process to prevent sublimation of vitreous water. All images were recorded by a SIS Megaview III wide-angle CCD camera.

UV-Vis Absorption

UV-vis absorption spectra were collected using a Cary 60 UV-vis spectrophotometer from Agilent Technologies. Solutions or gels were measured in a 2 mm pathlength quartz cuvette (Hellma Analytics). Spectra were collected from 380-1100 nm at a scan rate of 2 nm/s. For irradiated samples, the cuvettes were irradiated using a 365 nm 700 mA LED, giving around 70 mW intensity of light on the samples, which was measured using a photometer (Thor Labs). Samples were irradiated for 5 minutes before the spectra were collected. Samples were allowed to relax back to the original colour before another spectrum was collected.

Spectroelectrochemistry

Spectra were collected using the spectrophotometer used above and a LabOmak UF-spectroelectrochemical cell. The cell has a platinum working and counter electrode. A PalmsSens4 potentiostat (Alvatek Ltd.) was used to control the voltage of the cell. To reduce the sample a potential of +0.7 V was applied for 60 seconds and a spectrum recorded. To then oxidise the sample, a potential of +0.6 V was applied for 2 minutes and a spectrum recorded. This was then cycled over 30-50 times to gauge the reversibility of the process.

Cyclic Voltammetry

CVs were collected using a PalmSens4 potentiostat with a glassy carbon working electrode, platinum counter electrode and an Ag/AgCl reference. Voltammograms were measured from 0 V to −1.5 V to +1 V at various scan rates from 0.02 V/s to 0.8 V/s. Voltammetry could be also used on the ITO windows to change the colour of the windows, with the reference and counter electrode on one end and the working electrode on the other. Alternatively, the potential could be set to −0.7 V for the dark colour and +0.6 V for the transparent colour.

Windows

The windows used for the chromic displays were prepared from FTO glass (TEC 10 20×15×1.1 mm, from Ossila). The glass was sonicated in ethanol at 40° C. for 30 mins prior to assembly and gloves were used throughout to prevent fingerprints on the glass. Two pieces of FTO glass were sandwiched together using a two-part epoxy resin and a 3D printed 1 mm thick spacer ensuring that the FTO layers were facing inside the cell. To be able to inject the gelator solution into the cell, two 0.8 mm diameter holes were drilled into one of the pieces of FTO glass. These could be sealed with glue or grease to prevent air getting into the cell. Pieces of copper tape were added to the edges of the cell to ensure good contact between the cell and the crocodile clips from the potentiostat. The working electrode was clipped to one end of the cell and the reference and counter electrodes to the other to make it a two-electrode experiment. The potential could be set to change the colour of the cell.

Solution and Gel Testing

The solution and gels prepared using the above protocol were tested for colour change and other physical properties.

Figure 2:
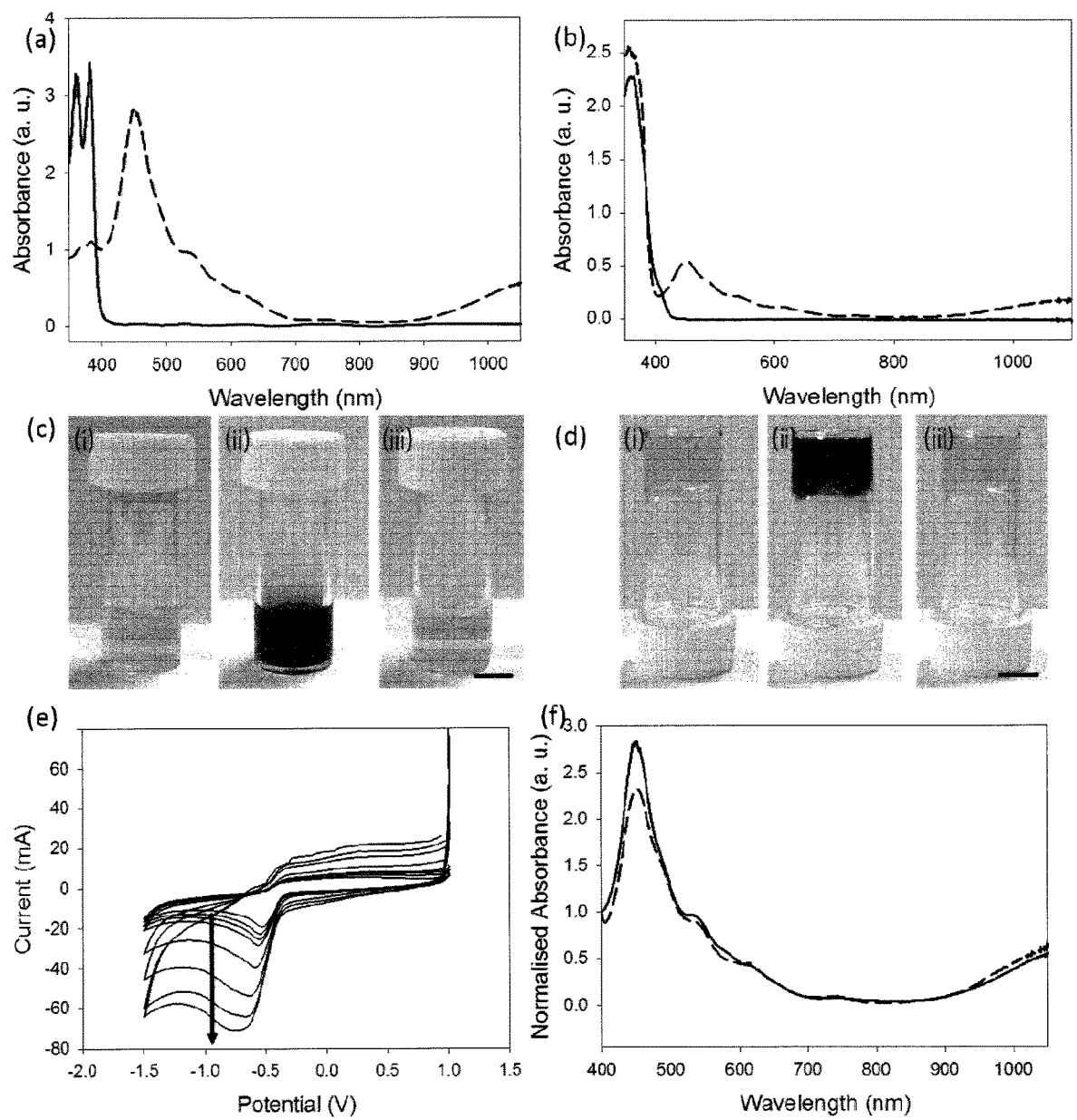
FIG. 2 shows data from the formation of the radical anion. (a) UV-Vis absorption spectra for a solution of 1 in water/glycerol. The continuous line is the absorption spectra for the solution as prepared, and dashed line is the absorption spectra for the mixture after irradiation with a 365 nm LED for 5 minutes; (b) UV-Vis spectra for gels of 1 in water/glycerol. The continuous line is the absorption spectra for the gel as prepared and the dashed line is the gel are after irradiation with a 365 nm LED for 5 minutes. (c) Photograph of (from left to right) a solution of 1 as formed, a solution of 1 just after irradiation with a 365 nm LED and after recovered. (d) a gel of 1 as prepared, and a gel of 1 after irradiation and after recovery. For (c) and (d), the scale bar represents 1 cm. (e) CVs run at different scan rates from 0.02 to 0.8 V/s. The arrow shows the direction of increasing scan rates. (f) Electrochemically generated state (continuous line) compared to the photogenerated state (dashed line) for the solutions of 1.
Figure 3:
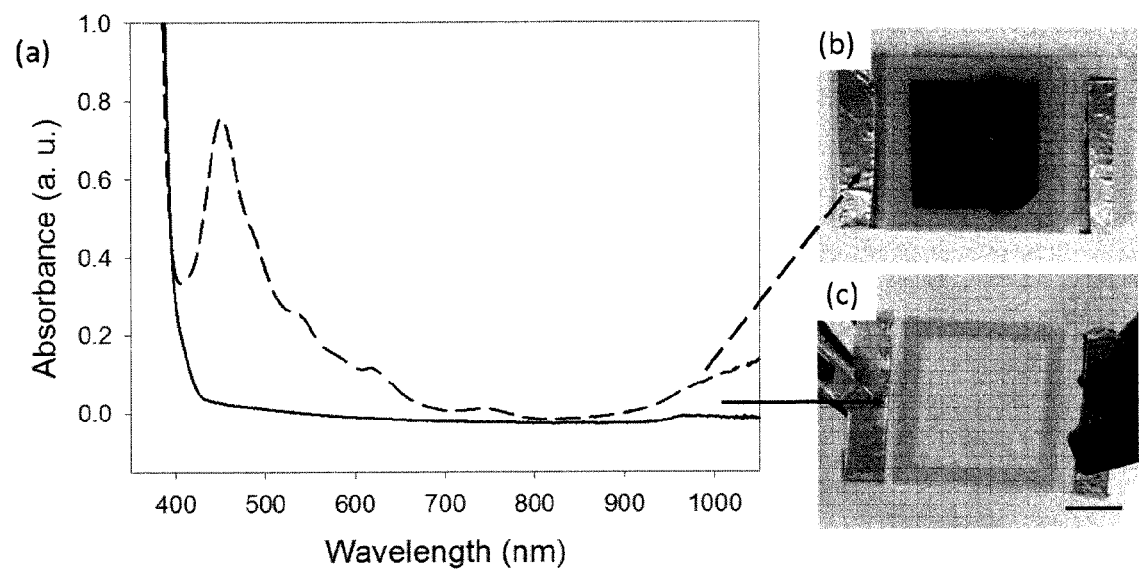
FIG. 3 shows UV-vis absorption data of a gel with compound 1 prepared in a cell irradiated with UV light (dashed line and (b)) and after applying 0.6 V for 60 seconds (continuous line and (c)). Scale bar is 1 cm.
Figure 4:
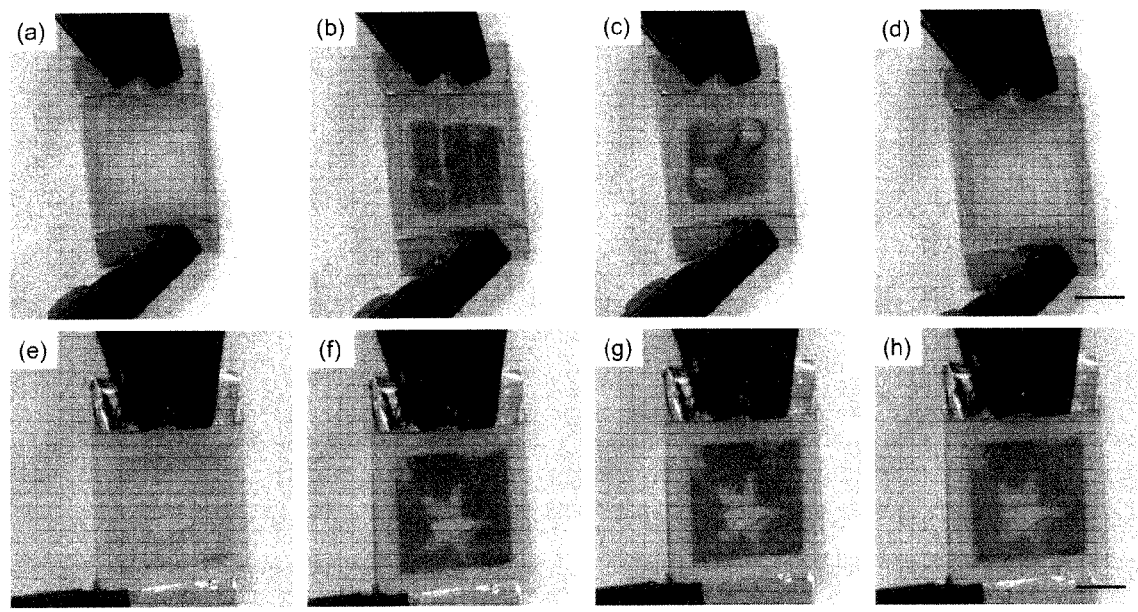
FIG. 4 shows images of patterned solutions and gels with compound 1. (a)-(d) Patterned solutions are not as stable over time as the gels (e)-(h) as shown by the loss of resolution on the patterned surface. (a) and (e) show the initial solution and gel, respectively. The photographs were taken over 10 minutes after applying a potential of 0.7 V. The scale bar represents 1 cm.

UV-Vis spectra were recorded according the above protocol. In water or water/glycerol mixtures as either solutions or gels, the absorption spectra are typical of an NDI, with a strong absorption below 400 nm (FIGS. 2a and b). The spectra only change in intensity on dilution, with no changes in peak position, implying that there are no changes in the self-assembled structure on dilution. Visually, the samples range from transparent to pale yellow as the concentration is increased and the thickness of the sample increases.

Photoreduction of compound 1 can be achieved using a 365 nm LED. On irradiation, both the solution and the gel containing compound 1 turn from the initial colour to very dark brown to black depending on the concentration of compound 1 and the duration and intensity of the irradiation (FIG. 2c).

This colour change can be linked to the formation of the radical anion, as shown by the presence of new peaks at 460 nm in the UV-Vis absorption spectra with a broad tail for both the solution and the gel (FIGS. 2a and b). There is no evidence of the dianion being formed from the UV-Vis absorption spectrum as shown by the absence of a peak at around 400 nm.

Figure 5:
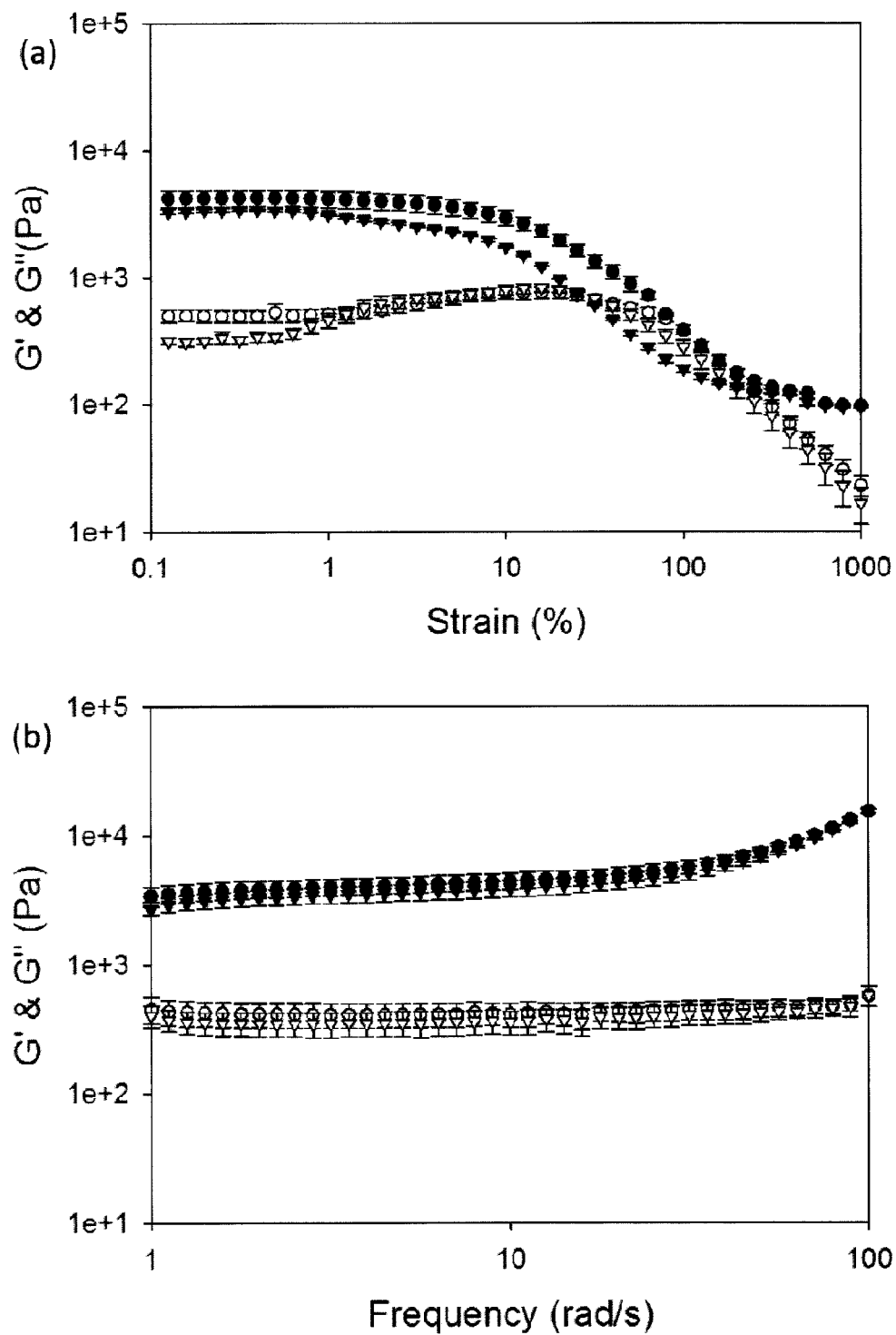
FIG. 5 shows rheological measurements of a gel of 1. (a) Strain sweep from 0.1-1000% strain at 10 rad/s. Before irradiation (circles), immediately after irradiation (triangles) showing a change in rheological strain behaviour (where the filled symbols relate to G' and the unfilled symbols to G"). (b) Frequency sweep from 1-100 rad/s at 0.5% strain. Before irradiation (circles), immediately after irradiation (triangles) showing no significant change in G' and G" (where the filled symbols relate to G' and the unfilled symbols to G"). (c) Strain sweep from 0.1-1000% strain at 10 rad/s. Before irradiation (circles), immediately after irradiation (triangles) and recovered gel (squares) showing the gel recovers its original properties (where the filled symbols relate to G' and the unfilled symbols to G"). All rheological measurements were carried out in triplicate at 25° C. and error bars plotted using standard deviation.
Figure 5:
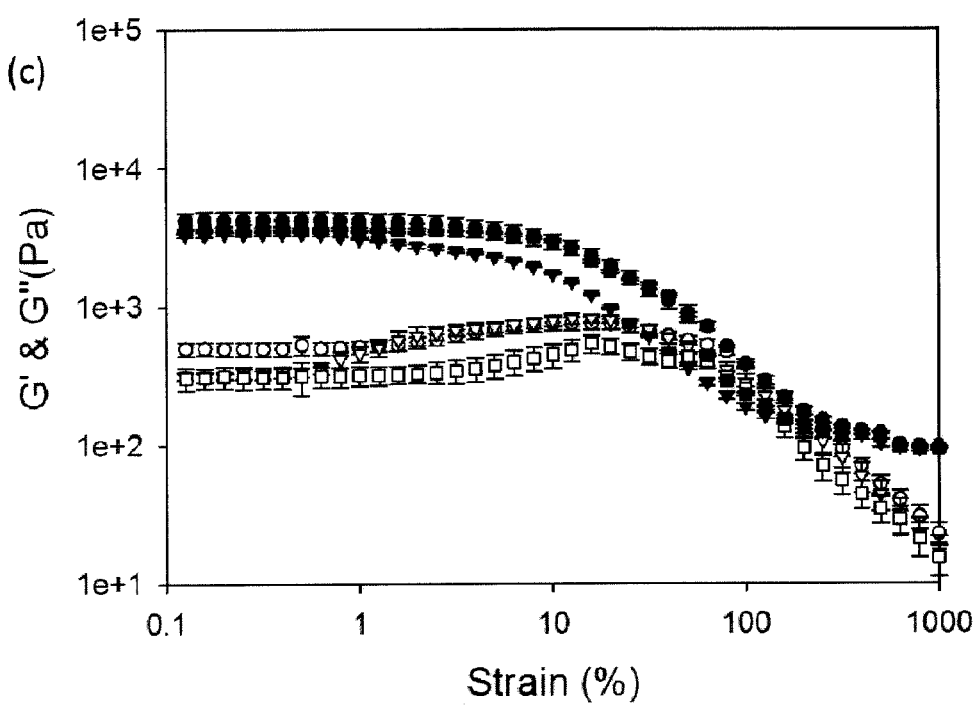

Generation of the radical anion does not result in the gel being destroyed. Unusually, the gels became stronger on irradiation. Here, on irradiation of a gel of compound 1, the absolute values of the storage and loss modulus do not change significantly (FIG. 5). However, the strain at which the gel breaks increases.

The SANS data for the solutions (FIG. 1d) and gels (FIG. 1f) after irradiation show slight changes. Over time, the solution returns to its original color, and the SANS data return to being almost identical to the as-prepared sample (FIG. 1d).

Figure 6:
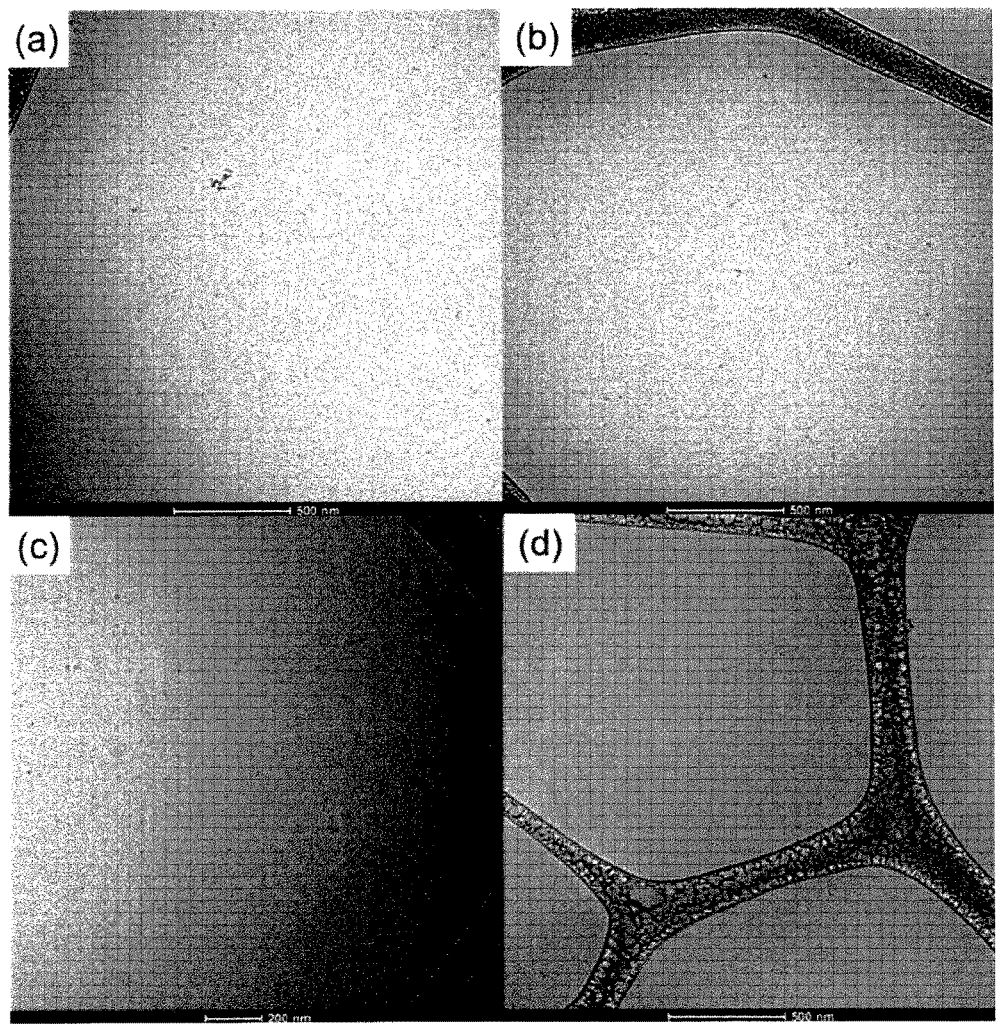
FIG. 6 shows Cryo-TEM images for a solution of 1 in water/glycerol at pH 8 containing 0.1 M NaCl. For (c), the scale bar represents 200 nm. In all other cases, the scale bar represents 500 nm.
Figure 7:
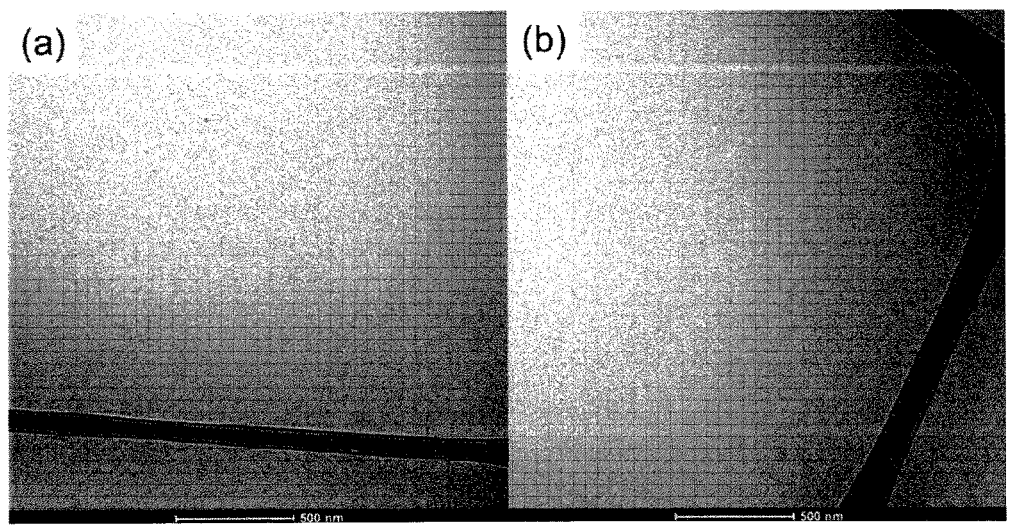
FIG. 7 shows Cryo-TEM images for a solution of 1 in water/glycerol at pH 8 containing 0.1 M NaCl after irradiation with a 365 nm LED. The scale bar represents 500 nm.

Cryo-TEM before irradiation shows the presence of spheres (FIG. 6). After irradiation, the cryo-TEM shows the presence of spheres as for before irradiation (FIG. 7).

Figure 8:
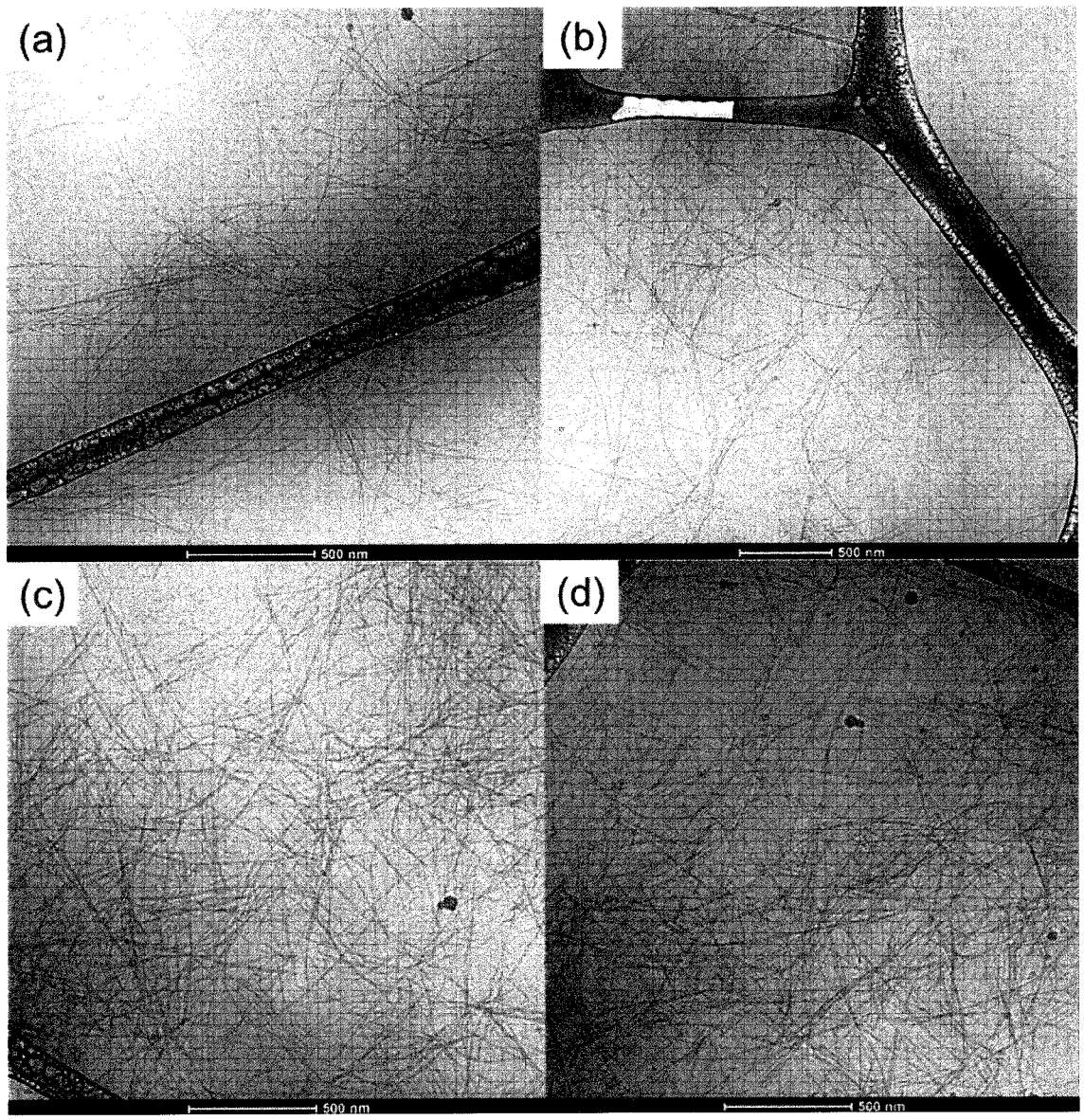
FIG. 8 shows Cryo-TEM images for a gel of 1 in glycerol/water at pH 3.4 containing 0.1 M NaCl. In all cases, the scale bar represents 500 nm.
Figure 9:
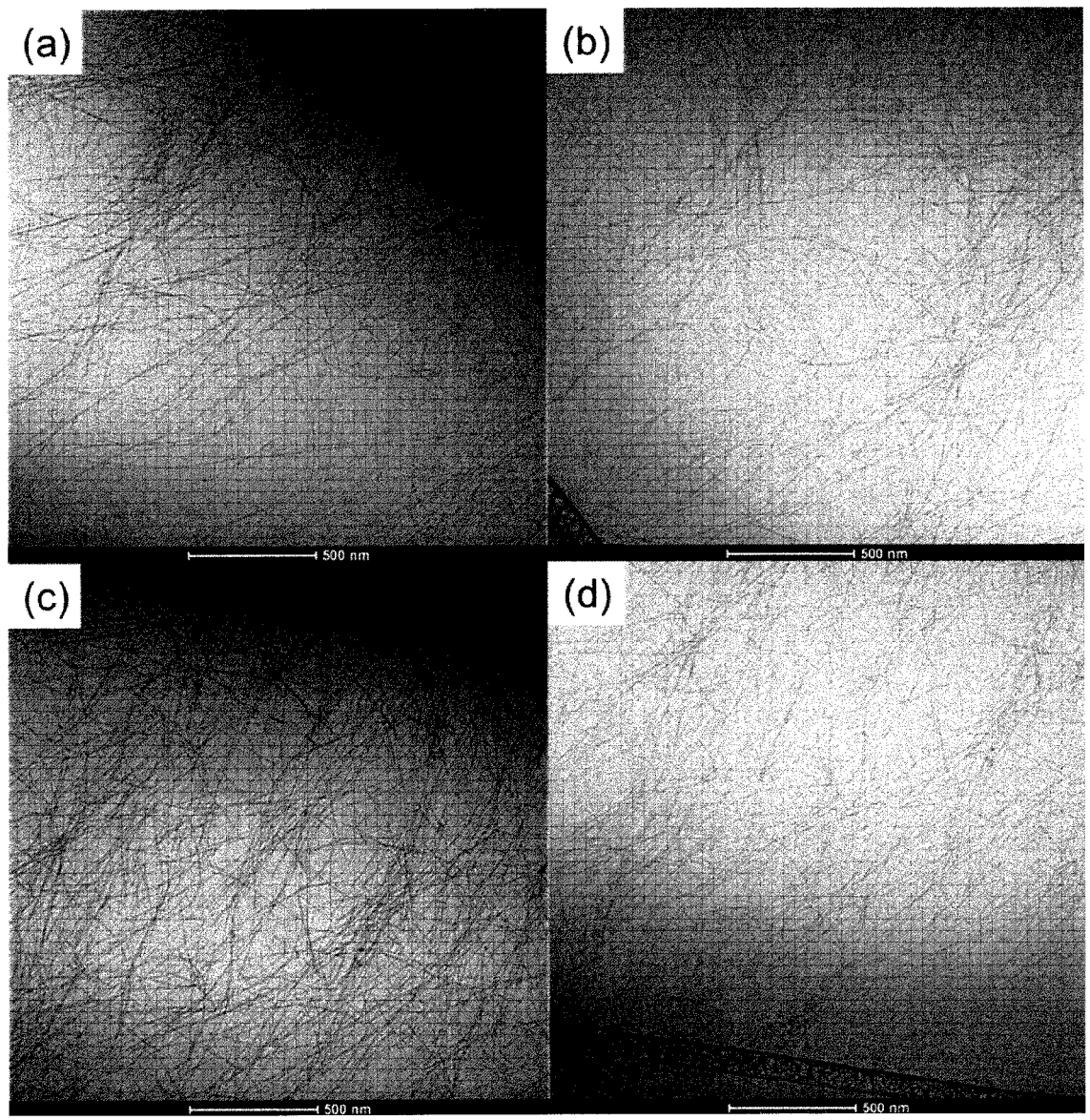
FIG. 9 shows Cryo-TEM images for a gel of 1 in water/glycerol at pH 3.4 containing 0.1 M NaCl after irradiation with a 365 nm LED. The scale bar represents 500 nm.

For the gels, Cryo-TEM shows that fibers are present before irradiation (FIG. 8). After irradiation, the fibers are very similar to those before irradiation (FIG. 9). Again, the data after the gel has returned to the original color are essentially identical to those as prepared.

Figure 10:
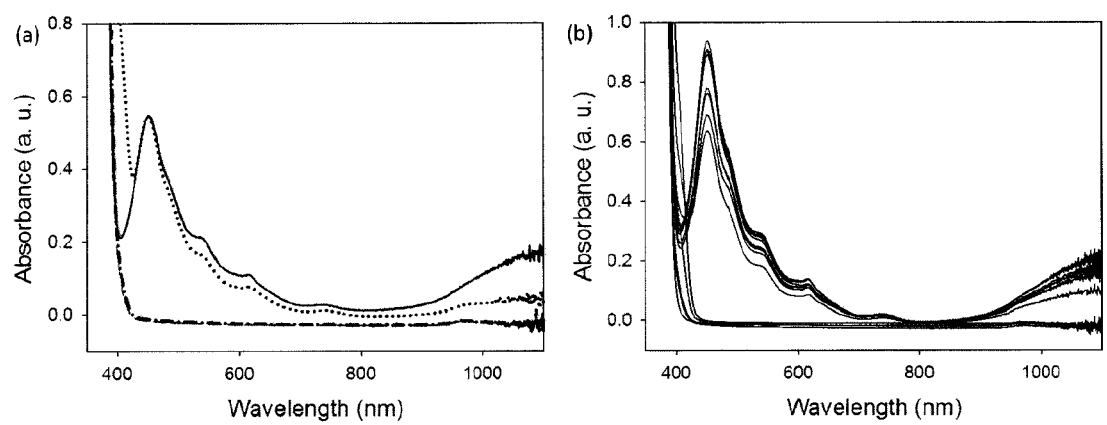
FIG. 10 shows UV-vis absorption data of a solution of 1 prepared in a spectroelectrochemical cell cycling between +0.6 V (dashed lines) and −0.7 V (solid lines and dotted lines). The black solid line relates to the $1^{st}$ cycle and the dotted line to the $50^{th}$ cycle. (b) Randomly selected spectra recorded during the 50 cycles showing little change in colour intensity between cycles.
Figure 11:
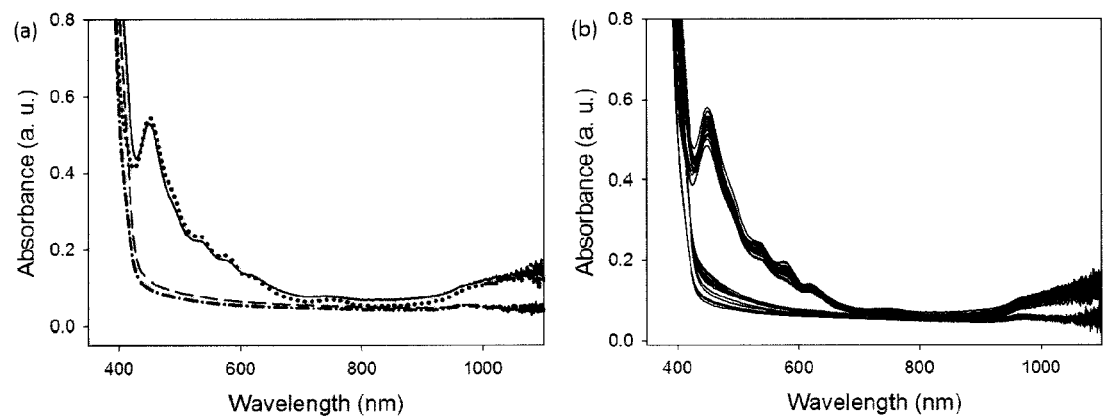
FIG. 11 shows UV-vis absorption data of a gel of 1 prepared in a spectroelectrochemical cell cycling between 0.6 V (dashed data) and −0.7 V (solid data). The black solid line relates to the $1^{st}$ cycle and the dotted line to the $30^{th}$ cycle. (b) 30 cycles showing little change in colour intensity during the cycles.

Importantly, the radical anion, and associated colour change, can also be generated electrochemically. The radical anion of 1 can be formed reversibly by a one-electron charge transfer processes as shown by cyclic voltammetry (FIGS. 10 and 11). The formation of the radical anion was confirmed using spectroelectrochemistry and the UV-Vis absorption spectra are very similar in both cases (FIG. 2f).

The generation of the radical anion and colour change can be achieved in both the solution and gel states.

Gel Patterning

Patterning was carried out by patterning the surface of the ITO glass (negative patterning). This was done by scratching the ITO surface to remove the conductive coating but could also be achieved when depositing the ITO. The gels gave a more defined and stable shape (FIGS. 4e-h) whereas the solutions gave defined patterns too, but they were not stable and were removed by diffusion and oxidation of the solution (FIGS. 4a-d).

In the gel state, where 1 is assembled into essentially immobile fibres, mixing by diffusion is not observed. This lack of diffusion allows more effective patterning of the gels.

Temperature Testing

Figure 12:
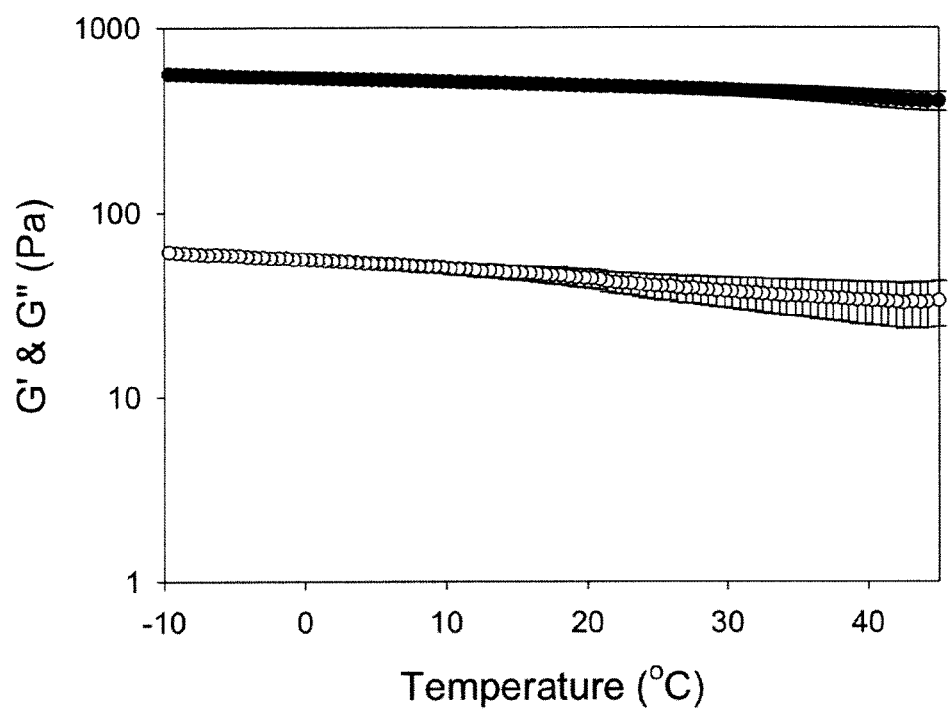
FIG. 12 shows rheological measurements of a gel of 1 at different temperatures. The temperature sweep rheology data collected at 0.5% strain and 10 rad/s from 45° C. to −10° C. showing no freezing or change in rheological properties over the temperature range. Data was collected in triplicate and error bars indicate a single standard deviation of the 3 repeat measurements. The filled symbols relate to G' and the unfilled symbols to G".

For use in many situations, the temperature range of the gels is important. The gels formed in a mixture of water and glycerol are stable over at least a temperature range of −10 to 45° C. (see FIG. 12).

Window Testing

The colour change from transparent to dark that was possible with solutions and gels of compound 1 suggests applications in electrochromic windows. A sandwich cell from FTO glass was contrasted according to the above protocol.

Irradiation of the cells with a 365 nm LED resulted in both solutions and gels turning a black colour (FIG. 2d). Leaving the cell in sunlight resulted in the gels and solution changing to a brown colour over several hours.

Forming the radical anion electrochemically resulted in a very quick change from transparent to black (less than 2 seconds for both the solution and the gel).

Figure 13:
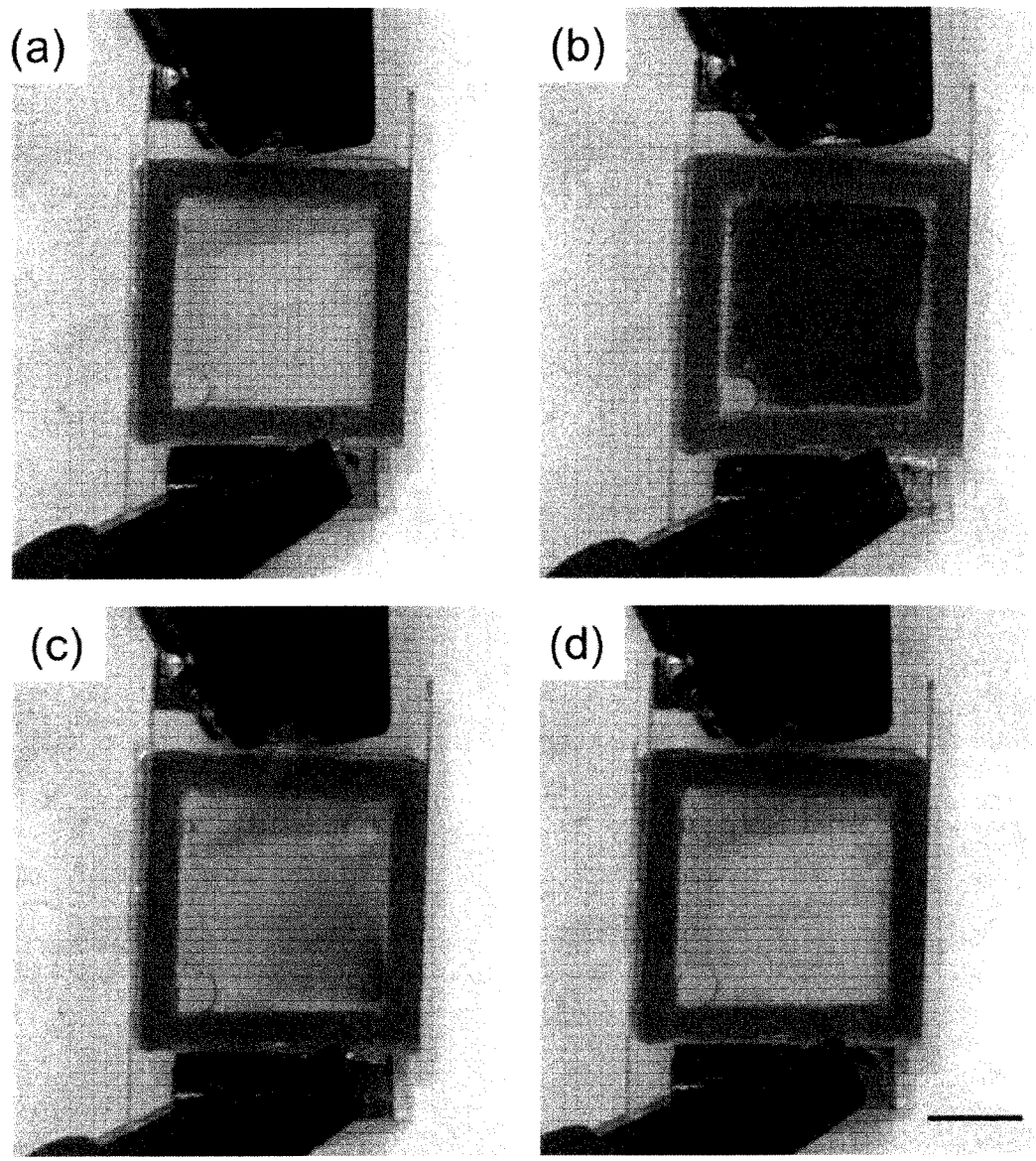
FIG. 13 shows electrochemically generated colour change for a gel of 1: (a) 0 V, (b) −0.7 V (c)+0.6 V and (d)+0.6 V after a minute. Scale bar represents 1 cm.

The reverse transition from black to transparent was slower, but still achieved in under 1 minute (FIG. 13).

This cycling between transparent to black could be carried out reversibly, for at least 30 cycles, with very little change in the colour as seen in the UV-vis absorption spectra of either the dark or the transparent state (FIGS. 10 and 11).

REFERENCES

All documents mentioned in this specification are incorporated herein by reference in their entirety.
Al Kobaisi et al., Chem. Rev. 2016, 116, 11685 to 11796.
Alkaabi et al., Chem 1., 2016, 264 to 272.
Doucet, M. et al. SasView version 4.1.2. (2017).
Zhang et al., Chem Mater., 2008, 20, 6163 to 6168.

The invention claimed is:
1. An electrochromic device comprising two electrodes, with a solution or a gel provided in the interelectrode space, wherein the solution or the gel comprises a solvent and a naphthalene diimide compound of Formula 1, or the salts and solvates thereof:

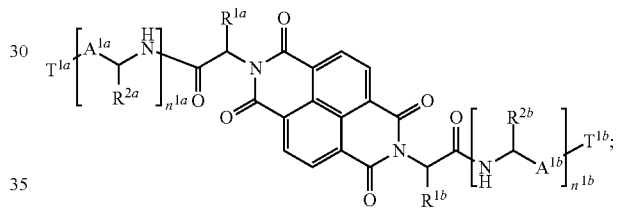

Formula 1 wherein:
$R^{1a}$ and $R^{1b}$ may be independently selected from hydrogen, benzyl, phenyl, $C_{1-6}$ alkyl, indolyl and —[C(O)—N(H)—CR'R"]$_m$—X, wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl; wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, and —NH—C(=NH)—NH$_2$;

$R^{2a}$ and $R^{2b}$ may be independently selected from hydrogen, benzyl, phenyl, $C_{1-6}$ alkyl, indolyl and —[C(O)—N(H)—CR'R"]$_m$—X, wherein each m is independently an integer from 1 to 5; R' and R" may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl; wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, and —NH—C(=NH)—NH$_2$;

each of -$A^{1a}$- and -$A^{1b}$- may be independently selected from —C(O)—, —C(=NR—CH$_2$— and a covalent bond where R is hydrogen or $C_{1-6}$ alkyl;

$T^{1a}$ and $T^{1b}$ may be independently selected from —OH, —NH$_2$, —NHMe, $C_{1-6}$ alkyl, phenyl and benzyl; and each of $n^{1a}$ and $n^{1b}$ is independently an integer from 0 to 5;

and wherein when $n^{1a}$ and $n^{1b}$ are each 0, at least one of $R^{1a}$ and $R^{1b}$ is not hydrogen.

2. The electrochromic device of claim 1, wherein the naphthalene diimide compound is a compound formula 1a; or the salts and solvates thereof:

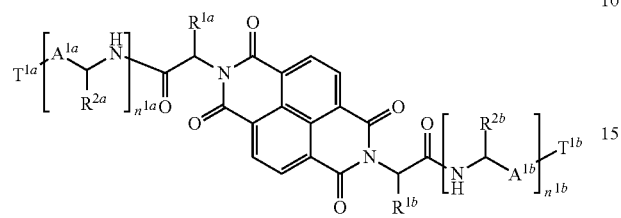

wherein:

$R^{1a}$ and $R^{1b}$ may be independently selected from hydrogen, benzyl, phenyl, $C_{1-6}$alkyl and indolyl wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, and —NH—C(=NH)—NH$_2$;

each of $n^{1a}$ and $n^{1b}$ is independently an integer from 1 to 5;

$R^{2a}$ and $R^{2b}$ may be independently selected from hydrogen, benzyl, phenyl, $C_{1-6}$alkyl and indolyl wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, and —NH—C(=NH)—NH$_2$;

each of -$A^{1a}$- and -$A^{1b}$- is independently selected from —C(O)—, —CH$_2$— and a covalent bond; and each of $T^{1a}$ and $T^{1b}$ is independently selected from —OH, —NH$_2$ and —NHMe.

3. The electrochromic device of claim 1, wherein in the naphthalene diimide compound each of $n^{1a}$ and $n^{1b}$ is 1.

4. The electrochromic device of claim 1, wherein in the naphthalene diimide compound each of $T^{1a}$ and $T^{1b}$ is —OH.

5. The electrochromic device of claim 1, wherein in the naphthalene diimide compound each of -$A^{1a}$- and -$A^{1b}$- is —C(O)—.

6. The electrochromic device of claim 1, wherein in the naphthalene diimide compound $R^{1a}$ and $R^{1b}$ are the same.

7. The electrochromic device of claim 1, wherein in the naphthalene diimide compound $R^{1a}$ and $R^{1b}$ are hydrogen.

8. The electrochromic device of claim 1, wherein in the naphthalene diimide compound $R^{2a}$ is the same as $R^{2b}$.

9. The electrochromic device of claim 1, wherein in the naphthalene diimide compound $R^{2a}$ and $R^{2b}$ are benzyl.

10. The electrochromic device of claim 1, wherein naphthalene diimide compound of Formula 1a is a compound of Formula 1aa:

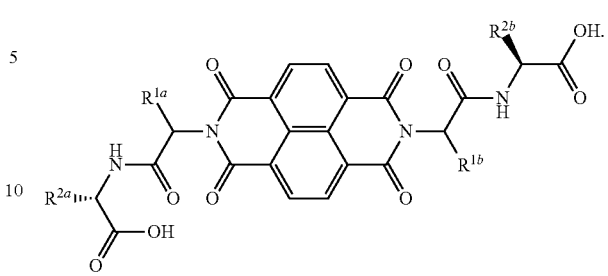

11. The electrochromic device of claim 1, wherein naphthalene diimide compound of formula 1a is selected from:

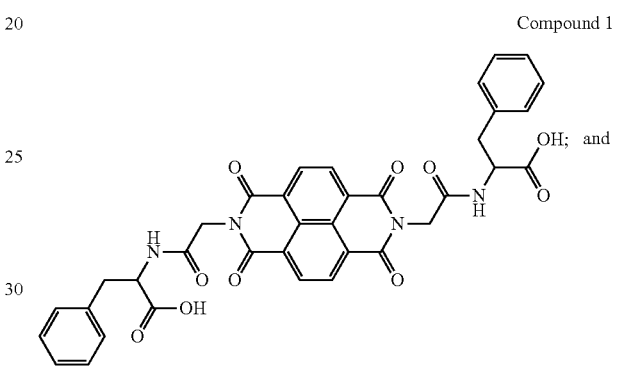

12. A naphthalene diimide compound selected from:

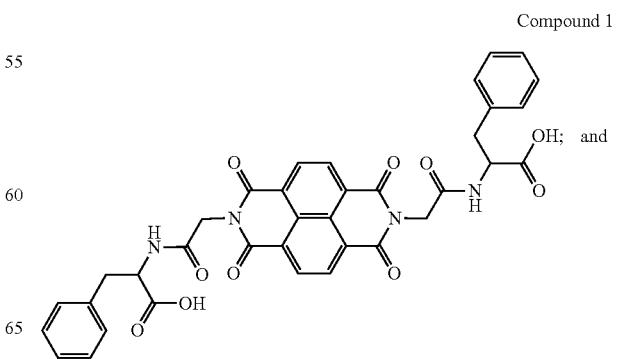

Compound 1a

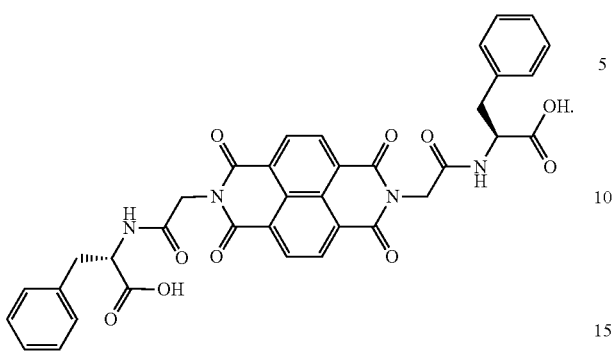

13. A gel comprising a naphthalene diimide compound according to claim 12 and a solvent.

14. The gel of claim 13, wherein the solvent is a mixture of water and glycerol.

15. The gel of claim 13, wherein the concentration of the naphthalene diimide compound in the gel is at least 0.4 mg/mL.

16. The gel of claim 13, wherein the pH of the gel is from 2 to 4.

17. The gel of claim 13, wherein the gel further comprises an acidifying agent preferably wherein the acidifying agent is glucono-δ-lactone (GdL).

18. A composition, comprising:
(i) a compound of Formula 1, or a salt or solvate thereof:

Formula 1

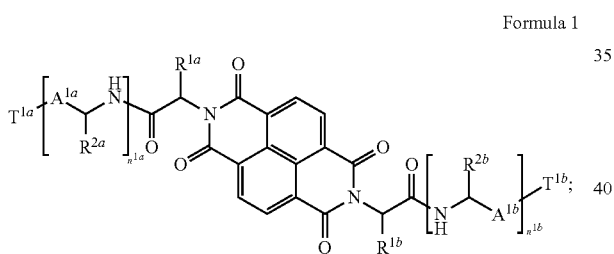

wherein:

$R^{1a}$ and $R^{1b}$ may be independently selected from hydrogen, benzyl, phenyl, $C_{1-6}$ alkyl, indolyl and —[C(O)—N(H)—CR'R'']$_m$—X; wherein each m is independently an integer from 1 to 5; R' and R'' may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl; wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, or —NH—C(=NH)—NH$_2$;

$R^{2a}$ and $R^{2b}$ may be independently selected from hydrogen, benzyl, phenyl, $C_{1-6}$ alkyl, indolyl and —[C(O)—N(H)—CR'R'']$_m$—X, wherein each m is independently an integer from 1 to 5; R' and R'' may be independently selected from hydrogen, benzyl, phenyl, $C_{1-6}$ alkyl and indolyl and X may be independently selected from —OH, —NH$_2$, —NHMe, $C_{1-6}$ alkyl, phenyl and benzyl; wherein the benzyl, phenyl, $C_{1-6}$ alkyl and indolyl may be optionally substituted with one or more groups selected from the group consisting of —OH, —F, —Cl, —Br, —SH, —SeH, —COOH, —NH$_2$, and —NH—C(=NH)—NH$_2$;

each of -$A^{1a}$- and -$A^{1b}$- may be independently selected from —C(O)—, —C(=NR)—CH$_2$— and a covalent bond where R is hydrogen or $C_{1-6}$ alkyl;

$T^{1a}$ and $T^{1b}$ may be independently selected from —OH, —NH$_2$, —NHMe, $C_{1-6}$ alkyl, phenyl and benzyl; and each of $n^{1a}$ and $n^{1b}$ is independently an integer from 0 to 5;

wherein when $n^{1a}$ and $n^{1b}$ are each 0, at least one of $R^{1a}$ and $R^{1b}$ is not hydrogen; and (ii) a solvent.

19. The composition of claim 18, wherein the solvent is a mixture of water and glycerol.

* * * * *